(12) United States Patent
Cirillo et al.

(10) Patent No.: US 7,041,669 B2
(45) Date of Patent: May 9, 2006

(54) 1,4-BENZOFUSED UREA COMPOUNDS USEFUL IN TREATING CYTOKINE MEDIATED DISEASES

(75) Inventors: Pier Francesco Cirillo, Woodbury, CT (US); Abdelhakim Hammach, Danbury, CT (US); John Robinson Regan, Larchmont, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 344 days.

(21) Appl. No.: 10/369,847

(22) Filed: Feb. 19, 2003

(65) Prior Publication Data

US 2003/0232865 A1 Dec. 18, 2003

Related U.S. Application Data

(60) Provisional application No. 60/359,809, filed on Feb. 25, 2002.

(51) Int. Cl.
*A61K 31/537* (2006.01)
*C07D 413/12* (2006.01)
*C07D 413/14* (2006.01)
*A61P 19/02* (2006.01)

(52) U.S. Cl. ............... 514/236.5; 544/58.2; 544/58.5; 544/79; 544/131; 544/140; 546/275.4; 546/256; 546/205; 548/312.4; 548/365.4

(58) Field of Classification Search ............ 514/236.5; 544/58.2, 58.5, 79, 131, 140; 546/275.4, 546/256, 205; 548/312.4, 365.4
See application file for complete search history.

(56) References Cited

U.S. PATENT DOCUMENTS

| | | | |
|---|---|---|---|
| 4,105,766 | A | 8/1978 | Alexander |
| 4,435,567 | A | 3/1984 | Lugosi et al. |
| 5,162,360 | A | 11/1992 | Creswell |
| 5,686,455 | A | 11/1997 | Adams et al. |
| 5,739,143 | A | 4/1998 | Adams et al. |
| 5,777,097 | A | 7/1998 | Lee et al. |
| 5,783,664 | A | 7/1998 | Lee et al. |
| 5,859,041 | A | 1/1999 | Liverton et al. |
| 5,869,043 | A | 2/1999 | McDonnell et al. |
| 5,871,934 | A | 2/1999 | Lee et al. |
| 5,916,760 | A | 6/1999 | Goeddel et al. |
| 5,948,885 | A | 9/1999 | Stein et al. |
| 6,242,453 | B1 | 6/2001 | Cirillo et al. |
| 6,319,921 | B1 | 11/2001 | Cirillo et al. |
| 6,344,476 | B1 | 2/2002 | Ranges et al. |

FOREIGN PATENT DOCUMENTS

| | | |
|---|---|---|
| DE | 293 352 | 8/1991 |
| EP | 0 272 866 | 6/1988 |
| EP | 0 395 144 | 10/1990 |
| EP | 0 418 071 | 3/1991 |
| EP | 0692483 | 1/1996 |
| EP | 0859054 | 8/1998 |
| EP | 0922762 | 6/1999 |
| EP | 0 955 293 | 10/1999 |
| JP | 61228444 | 10/1986 |
| WO | WO 93/24458 | 9/1993 |
| WO | WO 94/18170 | 8/1994 |
| WO | WO 94/22866 | 10/1994 |
| WO | WO 96/25157 | 8/1996 |
| WO | WO 96/40143 | 12/1996 |
| WO | WO 97/16442 | 5/1997 |
| WO | WO 97/22704 | 6/1997 |
| WO | WO 97/33883 | 9/1997 |
| WO | WO 97/35855 | 10/1997 |
| WO | WO 97/35856 | 10/1997 |
| WO | WO 97/44467 | 11/1997 |
| WO | WO 97/47618 | 12/1997 |
| WO | WO 97/48697 | 12/1997 |
| WO | WO 98/07425 | 2/1998 |
| WO | WO 98/15618 | 4/1998 |
| WO | WO 98/27098 | 6/1998 |
| WO | WO 98/52558 | 11/1998 |
| WO | WO 98/52559 | 11/1998 |
| WO | WO 99/00357 | 1/1999 |
| WO | WO 99/23091 | 5/1999 |

(Continued)

OTHER PUBLICATIONS

International Search Report Jun. 30, 2003.

(Continued)

*Primary Examiner*—James O. Wilson
*Assistant Examiner*—Paul V. Ward
(74) *Attorney, Agent, or Firm*—Michael P. Morris; Mary-Ellen M. Devlin; Anthony P. Bottino

(57) ABSTRACT

Disclosed are 1,4-disubstituted benzo-fused urea compounds of formula (I):

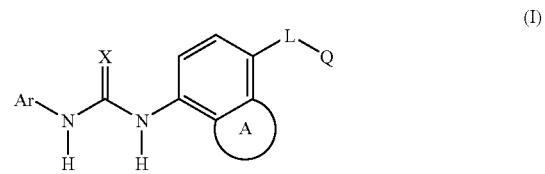

(I)

wherein Ar, X, A, L, and Q of formula(I) are defined herein. The compounds inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

4 Claims, No Drawings

FOREIGN PATENT DOCUMENTS

| | | |
|---|---|---|
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/32463 | 7/1999 |
| WO | WO 99/46244 | 9/1999 |
| WO | WO 00/41698 | 7/2000 |
| WO | WO 00/43384 | 7/2000 |
| WO | WO 00/55139 | 9/2000 |
| WO | WO 00/55152 | 9/2000 |
| WO | WO 01/04115 A2 * | 1/2001 |
| WO | WO 01/36403 | 5/2001 |
| WO | WO 02/066442 | 8/2002 |
| WO | WO 02/083628 | 10/2002 |
| WO | WO 02/092576 | 11/2002 |
| WO | WO 02/096876 | 12/2002 |
| WO | WO 02/098869 | 12/2002 |
| WO | WO 03/005999 | 1/2003 |

OTHER PUBLICATIONS

Polmar. S. et al: Safety and Pharmacokinetics of an oral p38 MAP Kinase Inhibitor (BIRB 796 BS), Administered twice daily for 14 days to healthy volunteers. Journal of Allergy and Clinical Immunology Online, Jan. 2002, Part 2, vol. 109, No. 1.

Gupta, A. et al: Safety, Pharmacokinetics and Pharmacodynamics of single doses of an oral p38 MAP Kinase Inhibitor (BIRB 796 BS) in healthy human males a placebo-controlled, randomized study, double blinded at each dose level. 58th Ann Mtg of the American Academy of Allergy, Asthma and Immunology, (AAAAI), New York, Mar. 1-6, 2002, J. Allergy Clin Immun. 2002, 109(1) Sup: S67.

Wood, Chester C. et al : Safety, Pharmacokinetics and Pharmacodynamics of an Oral p38 MAP Kinase Inhibitor (BIRB 796 BS), Administered Once Daily for 7 days. Journal of Allergy and Clinical Immunology Online, Jan. 2002, part 2, vol. 109, No. 1.

Zimmitti, C.S., et al: Suppression of p38 activity in vitro and TNF alpha production in vivo with BIRB 796 BS. A novel p38 kinase inhibitor, Arthritis Rheum 2001; ; 44(9):S114, A.

Schwartz, R. et al; Inhibition of p 38 MAP Kinase (MAPK) by BIRB 796 Attenuates Human Neutrophil Activation In Vivo and Inhibits their Influx in Vivo In a Mouse Model of Peritonitis; Arthritis Rheum 2001: 44(9):S114.

Branger, J. et al; Anti-inflammatory effects of a p38 Mitogen activated protein kinase inhibitor (BIRB 796 BS) during human endotoxemia. Arthritis Rheum 2001; 44(9): S164.

Nabozny, G. et al; Inhibition of Established collagen induced arthritis (C(A) with BIB 796, a selective inhibitor of p38 MAP Kinase, Arthritis Rheum 2001; 44(9):S368.

Madwed, J. et al; Pharmacological evaluation of BIRB 796, a selective inhibitor of p38 MAP Kinase (MAPK), in animal models of endotoxic shock, inflammation and arthritis. Inflammation 2001, 5th World Cong. on Inflammation, Edinburgh, Sep. 22-26, 2001 Inflamm Res. 2001;50 (Suppl 3):S184.

Pargellis, C. et al; A novel Series of p38 MAP Kinase Inhibitors: development of a clinical candidate, BIRB 796 Inflammation 2001, 5th World Cong. on Inflammation, Edinburgh, Sep. 22-26, 2001 Inflamm Res. 2001;50 (Suppl 3):S184.

Madwed, J. et al; An in vitro and ex vivo analysis of BIRB 796 BS, a p38 MAP Kinase (MAPK) inhibitor, on Neutrophils in Humans Inflammation 2001, 5th World Cong. on Inflammation, Edinburgh, Sep. 22-26, 2001 Inflamm Res. 2001;50 (Suppl 3):S184.

Branger, J. et al; Anti-inflammatory effects of a p38 mitogen-activated protein kinase inhibitor during human endotoxemia. J Immunol 2002:168:4070-4077.

Torcellini, C., et al; Pharmacologial evaluation of BIRB 796, a selective inhibitor of p38 MAP Kinase (MAPK), in animal models of endotoxin shock, inflammation and arthritis. Experimental Biol. 2002 Ann. Mta of Prof. Research Scientists, Apr. 20-24, 2002.

New Orleans FASEB J 2002;1695):A1081.

Mealy, N. et al; Dermatologic drugs. Drugs Future 2002; 27(3):289-291.

* cited by examiner

1,4-BENZOFUSED UREA COMPOUNDS USEFUL IN TREATING CYTOKINE MEDIATED DISEASES

APPLICATION DATA

This application claims benefit to U.S. provisional application No. 60/359,809 filed Feb. 25, 2002.

TECHNICAL FIELD OF THE INVENTION

This invention relates to 1,4-disubstituted benzo-fused urea compounds of formula(I):

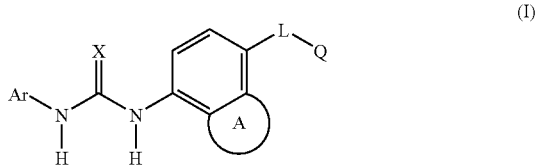

wherein Ar, X, A, L, and Q of formula(I) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

In PCT publications WO 00/55139 and WO 00/43384 there are described aromatic heterocyclic compounds useful in treating certain cytokine mediated diseases. Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, Rev. Infect. Disease 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, J. Invest. Med. 43: 28–38). Studies suggest that inflammatory changes mediated by cytokines may be involved in endothelial cell pathogenesis including restenosis after percutaneous transluminal coronary angioplasty (PTCA) (Tashiro, H., et al., March 2001, Coron Artery Dis 12(2):107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, British J. Rheum. 35: 334–342 and Stack, W. A., et al., 1997, Lancet 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, Nature Biotechnology 15: 1240). Another version of the TNFα receptor, Ro 45–2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, Inflamm. Res. 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, Nutrution 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, Biomed Pharmacother. 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, J Bone Miner Res. 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, Proc Soc Exp Biol Med. 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., Proc. Natl. Acad. Sci. U.S.A, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα0 and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3–12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.,* 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia.

Compounds which modulate release of one or more of the aforementioned inflammatory cytokines can be useful in treating diseases associated with release of these cytokines.

For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atroclerosis.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide novel 1,4-disubstituted benzo-fused urea compounds of formula (I):

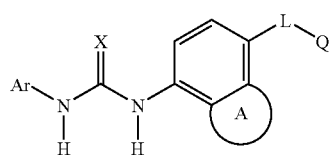

(I)

wherein Ar, X, A, L, and Q of formula(I) are defined below, which inhibit the release of inflammatory cytokines such as interleukin-1 and tumor necrosis factor.

It is a further object of the invention to provide methods for treating cytokine mediated diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In the broadest generic aspect of the invention, there are provided compounds of the formula (I):

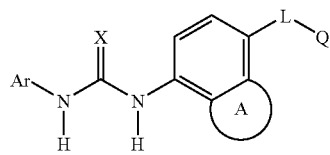

(I)

wherein
ring A is:
fused saturated or unsaturated ring containing 3–5 carbon atoms wherein ring A or the phenyl ring to which it is fused is optionally substituted by one or more $C_{1-6}$ branched or unbranched alkyl optionally partially or fully halogenated, acetyl, aroyl, $C_{1-6}$ branched or unbranched alkoxy optionally partially or fully halogenated, halogen, methoxycarbonyl, phenylsulfonyl, hydroxy, amino, mono- or di-($C_{1-4}$ alkyl)amino, mono- or di-($C_{1-4}$ alkyl) amino-S(O)$_2$, cyano, nitro or $H_2NSO_2$;

Preferred formula (I) compounds are those where ring A and the phenyl ring to which it is fused form:

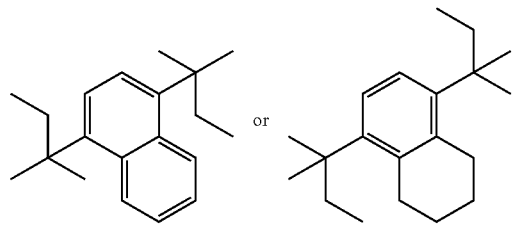

Ar is a heterocyclic group chosen from pyrrole, pyrrolidine, pyrazole, imidazole, oxazole, thiazole, furan and thiophene;

wherein Ar may be substituted by one or more $R_1$, $R_2$ or $R_3$;
L, a linking group, is:
—O—, —S(O)$_m$—, —NH— or
$C_{1-10}$ saturated or unsaturated branched or unbranched carbon chain;
wherein one or more methylene groups are optionally independently replaced by O, N or S, wherein said carbon chain is optionally substituted with 1–2 oxo groups and one or more $C_{1-4}$ branched or unbranched alkyl optionally substituted by one or more halogen atoms;
Q is chosen from:
phenyl, pyridine, pyrimidine, pyridazine, imidazole, benzimidazole, furan, thiophene, pyran, naphthyridine, 2,3-dihydrobenzo[1,4]oxazinyl, 2-oxa-5-aza-bicyclo[2.2.1] heptyl, oxazo[4,5-b]pyridine and imidazo[4,5-b]pyridine, tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone, wherein each Q is substituted by one to three Y;
$R_1$ is
a) phenyl, benzyl, naphthyl, morpholino, pyridinyl, pyrimidinyl, pyrazinyl, pyridazinyl, pyrrolyl, pyrrolidinyl, piperidinyl, imidazolyl, pyrazolyl, thiazolyl, oxazoyl, [1,3,4]oxadiazol, triazolyl, tetrazolyl, thienyl, furanyl, tetrahydrofuranyl, tetrahydropyranyl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pteridinyl, phthalazinyl, naphthypyridinyl, quinoxalinyl, quinazolinyl, purinyl or indazolyl, each of $R_1$ is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl$C_{0-2}$ alkyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$ alkyl) amino-$C_{1-5}$ alkyl, $C_{1-5}$ alkyl-S(O)$_m$, amino-S(O)$_m$, di-($C_{1-3}$alkyl)amino-S(O)$_m$, $C_{1-6}$ acyl, $C_{1-6}$alkoxy$C_{1-3}$ acyl or carboxy-mono- or di-($C_{1-5}$alkyl)-amino;

b) $C_{3-7}$ cycloalkyl$C_{0-5}$ alkyl, bicyclopentanyl, bicyclohexanyl or bicycloheptanyl, each optionally partially or fully halogenated and optionally substituted with one to three $C_{1-3}$ alkyl groups or $C_{1-3}$ alkoxy each optionally partially or fully halogenated;

c) cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups or $C_{1-3}$ alkoxy each optionally partially or fully halogenated;

d) $C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-S(O)$_m$—$C_{1-4}$ alkyl-;

e) $C_{1-6}$ alkyl or $C_{1-6}$ alkoxy each of which is branched or unbranched and optionally partially or fully halogenated or optionally substituted with $R_4$;

$R_2$, is a $C_{1-6}$ branched or unbranched alkyl optionally partially or fully halogenated, $C_{1-6}$ acyl, aroyl, $C_{1-4}$ branched or unbranched alkoxy, each optionally partially or fully halogenated, carboxy, nitrile, nitro, halogen, $C_{1-6}$ alkoxycarbonyl, $C_{1-6}$ alkyl-S(O)$_m$ optionally partially or fully halogenated, phenyl-S(O)$_m$, amino or aminocarbonyl wherein the N atom is optionally mono-or-disubstituted by $C_{1-6}$ branched or unbranched alkyl, $C_{1-6}$ acyl, phenyl or benzyl;

$R_3$ is a) cycloalkyl chosen from cyclopentanyl, cyclohexanyl, cycloheptanyl, bicyclopentanyl, bicyclohexanyl and bicycloheptanyl, each optionally be partially or fully halogenated and optionally substituted with one to three $C_{1-3}$ alkyl groups;

b) $C_{5-7}$ cycloalkenyl chosen from cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

or c) acetyl, aroyl, alkoxycarbonylalkyl or phenylsulfonyl;

each $R_4$ is independently:

hydrogen, nitrile, phenyl or $C_{1-4}$ alkyl optionally partially or fully halogenated;

Y is independently chosen from

Z-$NR_5R_6$ wherein Z is a bond, —(CH$_2$)$_{1-5}$—, —CH$_2$—C(O)— or —C(O)—, aryl$C_{0-3}$ alkyl, aryloxy$C_{0-3}$ alkyl and aryl$C_{1-3}$ alkoxy wherein each aryl ring is optionally substituted by one to two halogen, $C_{1-6}$ alkyl or $C_{1-6}$ alkoxy; or Y is chosen from heterocyclyl$C_{0-3}$ alkyl wherein the heterocyclyl is chosen from morpholinyl, piperazinyl, piperidinyl, pyrrolidinyl, tetrahydropyranyl and tetrahydrofuryl and heteroaryl$C_{0-3}$ alkyl wherein the heteroaryl is pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl;

each $R_5$ or $R_6$ is independently:

hydrogen, $C_{1-6}$ branched or unbranched alkyl, $C_{3-7}$ cycloalkyl$C_{0-3}$ alkyl, heterocyclyl$C_{0-3}$ alkyl wherein the heterocyclyl is chosen from morpholinyl, piperazinyl, piperidinyl, pyrrolidinyl, tetrahydropyranyl and tetrahydrofuryl, heteroaryl$C_{0-3}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl and indazolyl, $C_{1-6}$ alkylsulfonyl or aryl$C_{0-3}$ alkyl wherein the aryl ring is optionally substituted by one to two halogen, $C_{1-6}$ alkyl, $C_{1-6}$ alkoxy or heteroaryl wherein the heteroaryl is as hereinabove described in this paragraph, wherein each cycloalkyl, heterocyclyl and heteroaryl in this paragraph is optionally substituted by one to two halogen, $C_{1-6}$ alkyl, $C_{1-6}$ alkoxy, amido, aryl optionally halogenated, aroyl and $C_{1-6}$ alkylsulfonamido, and wherein $R_5$ and $R_6$ cannot simultaneously be hydrogen;

m is 0, 1 or 2;

and

X is O or S or the pharmaceutically acceptable acids or salts thereof.

A yet more preferred subgeneric aspect of the invention comprises compounds of the formula (I), as described in the immediate previous paragraph, wherein:

Ar is thiophene or pyrazole optionally substituted by one to three $R_1$, $R_2$ or $R_3$;

ring A and the phenyl ring to which it is fused form:

Q is chosen from phenyl, pyridine, pyrimidine, pyridazine, imidazole, benzimidazole, 2,3-dihydrobenzo[1,4]oxazinyl, 2-oxa-5-azabicyclo[2.2.1]heptyl, oxazo[4,5-b]pyridine, imidazo[4,5-b]pyridine, morpholine, thiomorpholine, thiomorpholine sulfoxide, thiomorpholine sulfone, piperidine, piperidinone and tetrahydropyrimidone, wherein each Q is substituted by one to three Y;

L is —O—, —S— or $C_{1-6}$ saturated or unsaturated branched or unbranched carbon chain wherein one or more methylene groups are optionally independently replaced by O, N or S; and wherein said linking group is optionally substituted with 1–2 oxo groups and one or more $C_{1-4}$ branched or unbranched alkyl optionally substituted by one or more halogen atoms;

$R_1$ is phenyl, morpholino, pyridinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, isoxazolyl, isothiazolyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$ alkyl)amino, mono- or di-($C_{1-3}$ alkyl) amino-$C_{1-5}$ alkyl, amino-$S(O)_2$ or di-($C_{1-3}$alkyl)amino-$S(O)_2$, $C_{3-7}$ cycloalkyl, bicyclopentanyl, bicyclohexanyl or bicycloheptanyl, each optionally partially or fully halogenated each optionally substituted with one to three $C_{1-3}$ alkyl groups or $C_{1-3}$ alkoxy each optionally partially or fully halogenated;

cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups or $C_{1-3}$ alkoxy each optionally partially or fully halogenated;

or $C_{1-6}$ alkyl branched or unbranched and optionally partially or fully halogenated;

$R_2$, is a $C_{1-6}$ branched or unbranched alkyl optionally partially or fully halogenated, $C_{1-6}$ acyl, aroyl, $C_{1-4}$ branched or unbranched alkoxy, each optionally partially or fully halogenated, carboxy, nitrile, nitro or halogen;

each Y is chosen from

Z—$NR_5R_6$ wherein Z is a bond, —$(CH_2)_{1-3}$—, —$CH_2$—C(O)— or —C(O)—, thienyl, phenyl, benzyl, phenethyl, phenoxymethyl, phenyl$CH_2(CH_3)$—, phenoxy and benzyloxy wherein each phenyl ring aryl is optionally substituted by one to two halogen, $C_{1-6}$ alkyl or $C_{1-6}$ alkoxy; or Y is chosen from heterocyclyl$C_{0-2}$ alkyl wherein the heterocyclyl is chosen from morpholinyl, piperazinyl, piperidinyl, pyrrolidinyl, tetrahydropyranyl and tetrahydrofuryl;

each $R_5$ or $R_6$ is independently:

hydrogen, $C_{1-4}$ branched or unbranched alkyl, $C_{3-6}$ cycloalkyl$C_{0-3}$ alkyl, heterocyclyl$C_{0-2}$ alkyl wherein the heterocyclyl is chosen from piperazinyl, piperidinyl, pyrrolidinyl, tetrahydropyranyl and tetrahydrofuryl, heteroaryl$C_{0-2}$ alkyl wherein the heteroaryl is chosen from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl, $C_{1-3}$ alkylsulfonyl, phenyl, phenyl-CH(CH_3)— or benzyl wherein each phenyl ring is optionally substituted by one to two halogen, $C_{1-6}$ alkyl, $C_{1-6}$ alkoxy or heteroaryl wherein the heteroaryl is as hereinabove described in this paragraph, and wherein each cycloalkyl, heterocyclyl and heteroaryl in this paragraph is optionally substituted by one to two halogen, $C_{1-6}$ alkyl, $C_{1-6}$ alkoxy, phenyl optionally halogenated, amido, benzoyl and $C_{1-4}$ alkylsulfonamido and X is O.

A yet further preferred subgeneric aspect of the invention comprises compounds of the formula (I), as described in the immediate previous paragraph, wherein:

Ar is pyrazole, ring A and the phenyl ring to which it is fused form:

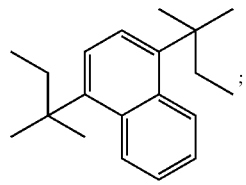

Q is chosen from phenyl, pyridine, pyrimidine, pyridazine, morpholine, thiomorpholine, thiomorpholine sulfoxide, thiomorpholine sulfone, piperidine, piperidinone, 2-oxa-5-aza-bicyclo[2.2.1]heptyl, 2,3-dihydrobenzo[1,4]oxazinyl, and tetrahydropyrimidone, wherein each Q is substituted by one to two Y;

L is:

—O—, —S—, >C(O), >C(S), —OCH_2—, —CH_2—, —CH_2CH_2—, —CH_2CH_2CH_2—, —C(CH_3)_2—, —CH(OH)—, —CH_2CH(OH)—, —CH(OH)CH_2—, —OCH_2CH_2—, —OCH_2CH_2CH_2—, —OCH_2CH(CH_3)—, —OCH_2(CH_3)CH_2—, —OCH_2C(O)—, —CH=CH—CH_2—, —CH=CHCH_2CH_2, —NH—, —NHCH_2—, —NHCH_2CH_2—, —S(O)_m—, —S(O)_mCH_2—, —S(O)_mCH_2CH_2— or —S(O)_mCH_2CH_2CH_2—;

$R_1$ is phenyl or pyridinyl optionally substituted with one to three $C_{1-6}$ branched or unbranched alkyl or $C_{1-3}$ alkoxy each of which is optionally partially or fully halogenated, $C_{3-7}$ cycloalkyl, bicyclopentanyl, bicyclohexanyl, bicycloheptanyl each optionally substituted with one to three $C_{1-3}$ alkyl groups or $C_{1-3}$ alkoxy each optionally partially or fully halogenated, halogen, hydroxy, oxo, nitrile, $C_{1-3}$ alkoxy optionally partially or fully halogenated, nitro, amino or mono- or di-($C_{1-3}$alky)lamino;

cyclopentenyl, cyclohexenyl, cycloheptenyl, cyclohexadienyl, cycloheptadienyl, bicyclohexenyl, bicycloheptenyl, each optionally substituted with one to three $C_{1-3}$ alkyl groups or $C_{1-3}$ alkoxy each optionally partially or fully halogenated;

or $C_{1-6}$ alkyl branched or unbranched and optionally partially or fully halogenated;

$R_2$, is a $C_{1-6}$ branched or unbranched alkyl, $C_{1-4}$ branched or unbranched alkoxy, each being optionally partially or fully halogenated, carboxy, nitrile, nitro, halogen;

each Y is chosen from

Z—$NR_5R_6$ wherein Z is a bond, —$(CH_2)_{1-2}$—, —$CH_2$—C(O)— or —C(O)—, thienyl, phenyl, benzyl, phenethyl, phenoxymethyl, phenyl$CH_2(CH_3)$—, phenoxy and benzyloxy wherein each phenyl ring aryl is optionally substituted by one to two halogen, $C_{1-6}$ alkyl or $C_{1-6}$ alkoxy; or Y is chosen from heterocyclyl$C_{0-2}$ alkyl wherein the heterocyclyl is chosen from morpholinyl, piperazinyl, piperidinyl, pyrrolidinyl, tetrahydropyranyl and tetrahydrofuryl;

each $R_5$ or $R_6$ is independently:

hydrogen, $C_{1-3}$ alkyl, $C_{3-6}$ cycloalkyl$C_{0-2}$ alkyl, heterocyclyl$C_{0-2}$ alkyl wherein the heterocyclyl is chosen from piperidinyl and tetrahydrofuryl, heteroaryl$C_{0-2}$ alkyl wherein the heteroaryl is chosen from pyridinyl, pyrimidinyl, pyrazinyl, pyridazinyl, thienyl and furyl, $C_{1-3}$ alkylsulfonyl, phenyl or phenyl-CH(CH$_3$)— wherein each phenyl ring is optionally substituted by one to two halogen, $C_{1-6}$ alkyl, $C_{1-6}$ alkoxy or heteroaryl wherein the heteroaryl is as hereinabove described in this paragraph, and wherein each cycloalkyl, heterocyclyl and heteroaryl in this paragraph is optionally substituted by one to two halogen, $C_{1-6}$ alkyl, $C_{1-6}$ alkoxy, acetamido, phenyl optionally halogenated, benzoyl and $C_{1-4}$ alkylsulfonamido.

A still yet further preferred subgeneric aspect of previous the invention comprises compounds of the formula (I), as described in the immediate paragraph, wherein Q is chosen from pyridine, pyrimidine, pyridazine, morpholine, 2-oxa-5-azabicyclo[2.2.1]hept-5-yl, 2,3-dihydrobenzo[1,4]oxazin-4-yl and piperidine, wherein each Q is substituted by one Y;

L is:
—O—, —S—, >C(O), —OCH$_2$—, —CH$_2$—, —CH$_2$CH$_2$—, —CH$_2$CH$_2$CH$_2$—, —CH(OH)—, —CH$_2$CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —S(O)$_m$—, —S(O)$_m$CH$_2$—, —S(O)$_m$CH$_2$CH$_2$— or —S(O)$_m$CH$_2$CH$_2$CH$_2$—;

R$_1$ is phenyl, pyridinyl, $C_{3-7}$ cycloalkyl, bicyclopentanyl, bicyclohexanyl, bicycloheptanyl, each optionally substituted with one to three $C_{1-3}$ alkyl groups or $C_{1-3}$ alkoxy each optionally partially or fully halogenated or $C_{1-6}$ alkyl branched or unbranched and optionally partially or fully halogenated;

each Y is chosen from

Z—NR$_5$R$_6$ wherein Z is a bond, —(CH$_2$)$_{1-2}$—, —CH$_2$—C(O)— or —C(O)—, thienyl, phenyl, benzyl, phenethyl, phenoxymethyl, phenylCH$_2$(CH$_3$)—, phenoxy and benzyloxy wherein each phenyl ring aryl is optionally substituted by one to two halogen, $C_{1-6}$ alkyl or $C_{1-6}$ alkoxy; or Y is chosen from heterocyclyl$C_{0-2}$ alkyl wherein the heterocyclyl is chosen from morpholinyl, piperazinyl, piperidinyl, pyrrolidinyl, tetrahydropyranyl and tetrahydrofuryl;

each R$_5$ or R$_6$ is independently:

hydrogen, $C_{1-3}$ alkyl, $C_{3-6}$ cycloalkyl$C_{0-2}$ alkyl, heterocyclyl$C_{0-2}$ alkyl wherein the heterocyclyl is chosen from piperidinyl and tetrahydrofuryl, heteroaryl$C_{0-2}$ alkyl wherein the heteroaryl is chosen from pyridinyl, pyrimidinyl, pyrazinyl, pyridazinyl, thienyl and furyl, $C_{1-3}$ alkylsulfonyl, phenyl or phenyl-CH(CH$_3$)— wherein each phenyl ring is optionally substituted by one to two halogen, $C_{1-6}$ alkyl, $C_{1-6}$ alkoxy or heteroaryl wherein the heteroaryl is as hereinabove described in this paragraph, and wherein each cycloalkyl, heterocyclyl and heteroaryl in this paragraph is optionally substituted by one to two halogen, $C_{1-6}$ alkyl, $C_{1-6}$ alkoxy, acetamido, phenyl optionally halogenated, benzoyl and $C_{1-4}$ alkylsulfonamido.

In a more particularly preferred embodiment

L is —O—, —S—, >C(O) or —OCH$_2$CH$_2$—;

Ar is

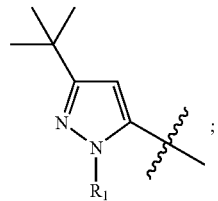

each Y is chosen from

Z—NR$_5$R$_6$ wherein Z is a bond, —CH$_2$—, —CH$_2$—C(O)— or —C(O)—, or Y is chosen from thienyl, phenyl, benzyl, phenethyl, phenoxymethyl, phenylCH$_2$(CH$_3$)— or piperidinyl$C_{0-1}$ alkyl;

each R$_5$ or R$_6$ is independently:

hydrogen, $C_{1-3}$ alkyl, $C_{3-6}$ cycloalkyl$C_{0-2}$ alkyl, heterocyclyl$C_{0-2}$ alkyl wherein the heterocyclyl is chosen from piperidinyl and tetrahydrofuryl, heteroaryl$C_{0-2}$ alkyl wherein the heteroaryl is chosen from pyridinyl, thienyl and furyl, $C_{1-3}$ alkylsulfonyl, phenyl or phenyl-CH(CH$_3$)—, wherein each cycloalkyl, heterocyclyl and heteroaryl in this paragraph is optionally substituted by one to two halogen, $C_{1-6}$ alkyl, $C_{1-6}$ alkoxy, acetamido, phenyl optionally halogenated, benzoyl and $C_{1-4}$ alkylsulfonamido.

In another preferred embodiment:

Ar is

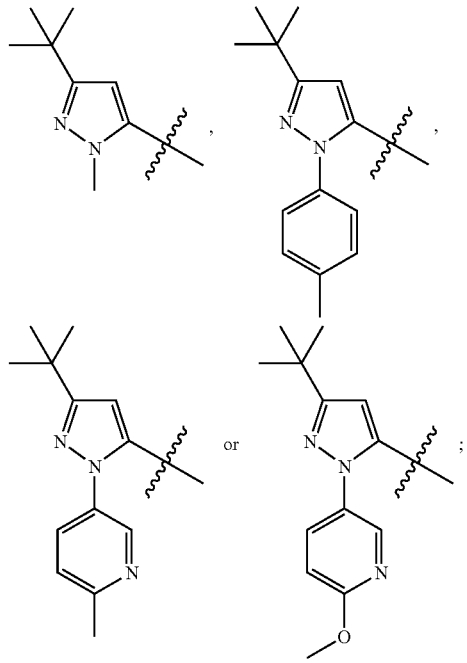

Y is chosen from

Z—NR$_5$R$_6$ wherein Z is a bond, —CH$_2$—, —CH$_2$—C(O)— or —C(O)—, or Y is phenyl, benzyl, phenethyl, phenoxymethyl, phenylCH$_2$(CH$_3$)—, thienyl or piperidinylmethyl;

each R$_5$ or R$_6$ is independently:

hydrogen, $C_{1-3}$ alkyl, $C_{3-6}$ cycloalkylmethyl, heterocyclyl$C_{0-2}$ alkyl wherein the heterocyclyl is chosen from piperidinyl and tetrahydrofuryl, heteroaryl$C_{0-2}$ alkyl wherein the heteroaryl is chosen from pyridinyl, thienyl and furyl, $C_{1-3}$ alkylsulfonyl, phenyl or phenyl-CH($CH_3$)—.

In yet another preferred embodiment

Y is chosen from

Z—$NR_5R_6$ wherein Z is a bond, —$CH_2$—, —$CH_2$—C(O)— or —C(O)—, or Y is phenyl, benzyl, phenethyl, phenoxymethyl, phenyl$CH_2(CH_3)$—, thien-2yl or piperidinylmethyl;

each $R_5$ or $R_6$ is independently:

hydrogen, $C_{1-2}$ alkyl, $C_{3-5}$ cycloalkylmethyl, piperidinylmethyl, tetrahydrofurylmethyl, pyridinyl-CH($CH_3$)—, thienylmethyl, $C_{1-3}$ alkylsulfonyl, phenyl or phenyl-CH($CH_3$)—.

The following compounds are representative of the compounds of formula(I):

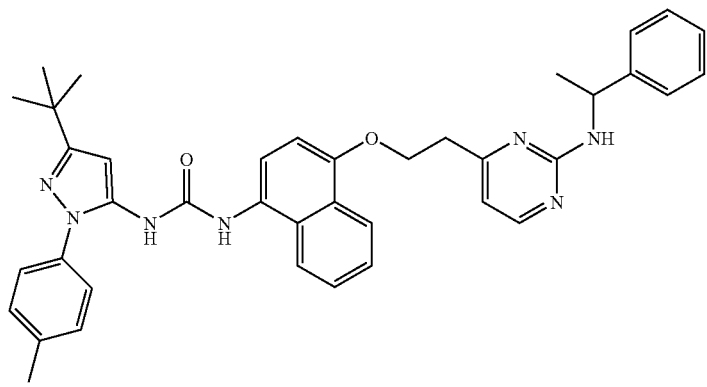

1-(5-tert-Butyl-2-p-tolyl-2H-pyrazol-3-yl)-3-(4-{2-[2-(1-phenyl-ethylamino)-pyrimidin-4-yl]-ethoxy}-naphthalen-1-yl)-urea;

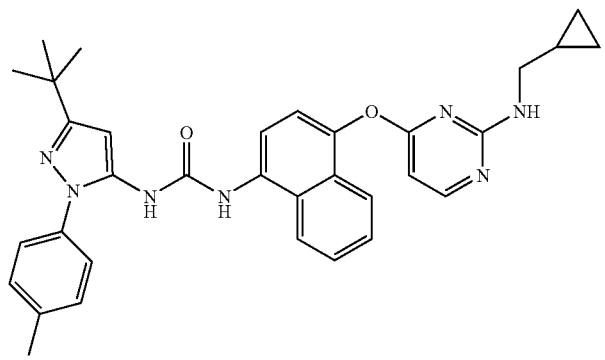

1-(5-tert-Butyl-2-p-tolyl-2H-pyrazol-3-yl)-3-{4-[2-(cyclopropylmethyl-amino)-pyrimidin-4-yloxy]-naphthalen-1-yl}-urea;

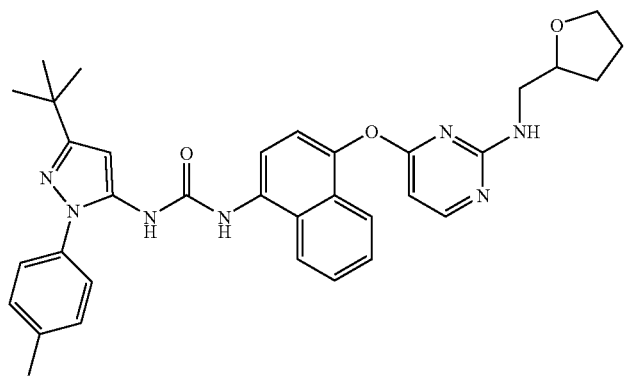

1-(5-tert-Butyl-2-p-tolyl-2H-pyrazol-3-yl)-3-(4-(2-[(tetrahydro-furan-2-ylmethyl)-amino]-pyrimidin-4-yloxy}-naphthalen-1-yl)-urea;

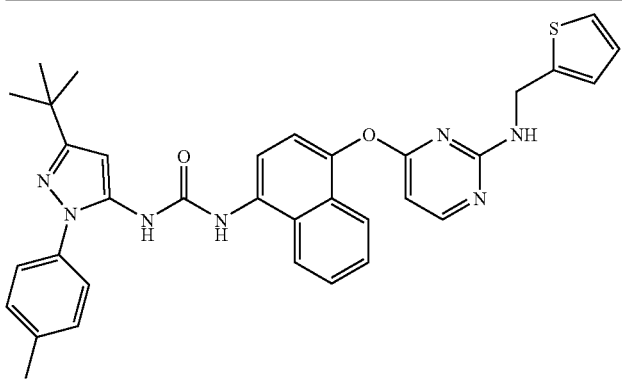

1-(5-tert-Butyl-2-p-tolyl-2H-pyrazol-3-yl)-3-(4-{2-[(thiophen-2-ylmethyl)-amino]-pyrimidin-4-yloxy}-naphthalen-1-yl)-urea;

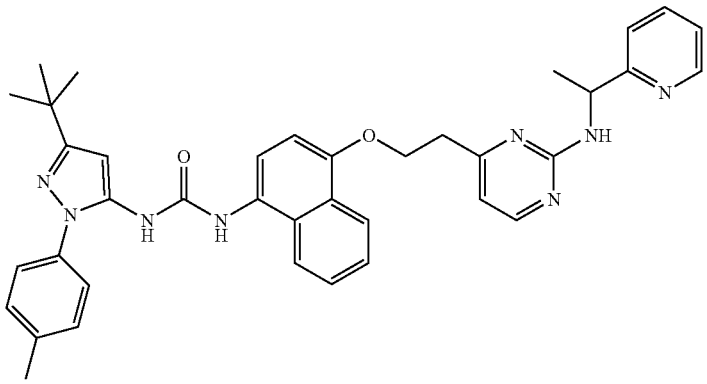

1-(5-tert-Butyl-2-p-tolyl-2H-pyrazol-3-yl)-3-(4-{2-[2-(1-pyridin-2-yl-ethylamino)-pyrimidin-4-yl]-ethoxy}-naphthalen-1-yl)-urea;

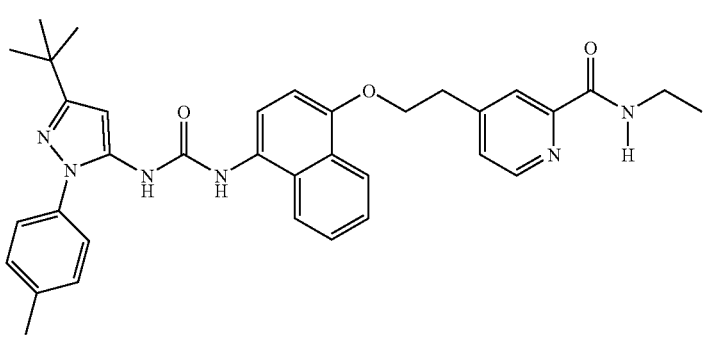

4-(2-{4-[3-(5-tert-Butyl-2-p-tolyl-2H-pyrazol-3-yl)-ureido]-naphthalen-1-yloxy}-ethyl)-pyridine-2-carboxylic acid ethylamide;

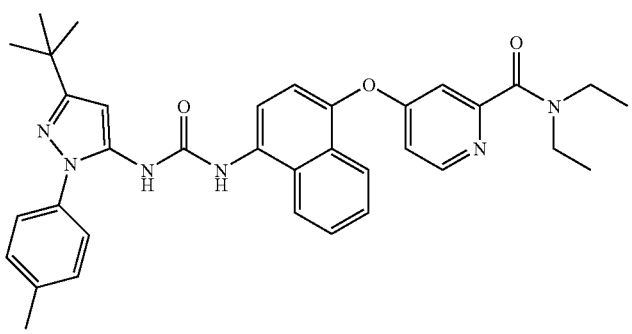

4-{4-[3-(5-tert-Butyl-2-p-tolyl-2H-pyrazol-3-yl)-ureido]-naphthalen-1-yloxy}-pyridine-2-carboxylic acid diethylamide;

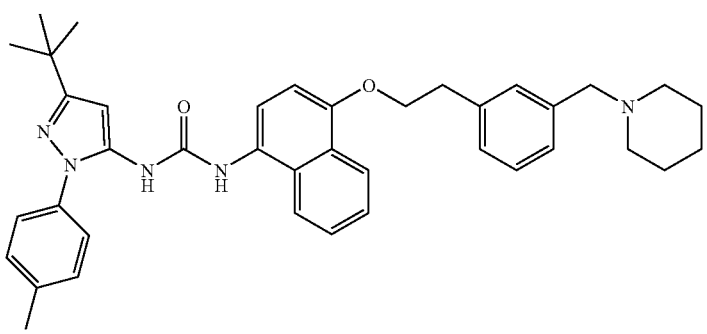

1-(5-tert-Butyl-2-p-tolyl-2H-pyrazol-3-yl)-3-{4-[2-(2-piperidin-1-ylmethyl-pyridin-4-yl)-ethoxy]-naphthalen-1-yl}-urea;

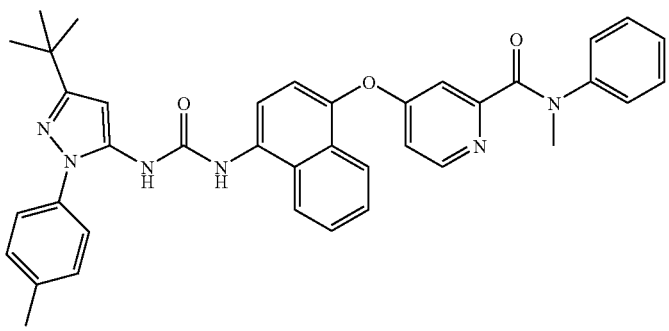

4-(4-{3-[5-tert-Butyl-2-(6-methyl-pyridin-3-yl)-2H-pyrazol-3-yl]-ureido}-naphthalen-1-yloxy)-pyridine-2-carboxylic acid methyl-phenyl-amide;

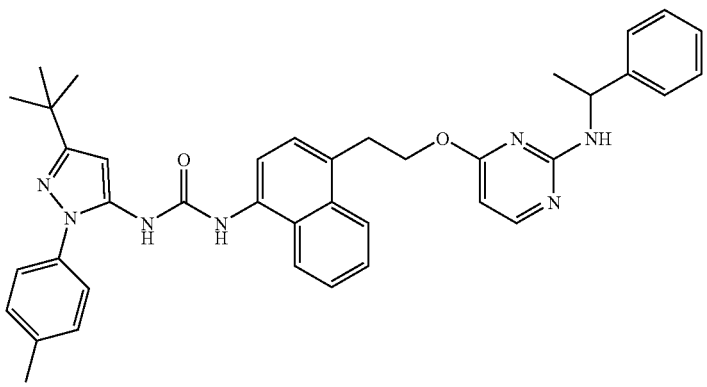

1-(5-tert-Butyl-2-p-tolyl-2H-pyrazol-3-yl)-3-(4-{2-[2-(1-phenyl-ethylamino)-pyrimidin-4-yloxy]-ethyl}-naphthalen-1-yl)-urea;

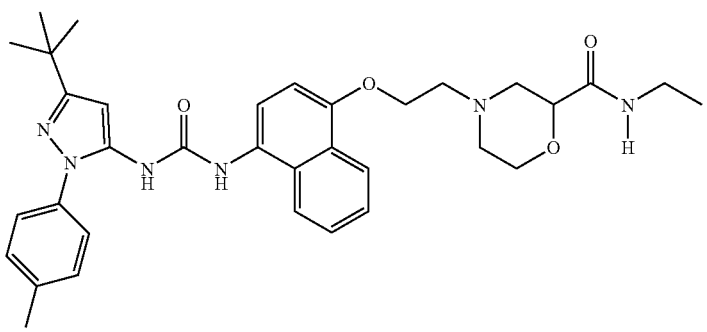

4-(2-{4-[3-(5-tert-Butyl-2-p-tolyl-2H-pyrazol-3-yl)-ureido]-naphthalen-1-yloxy}-ethyl)-morpholine-2-carboxylic acid ethylamide;

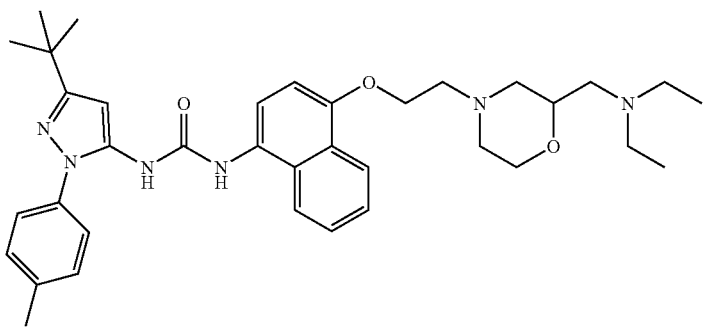 1-(5-tert-Butyl-2-p-tolyl-2H-pyrazol-3-yl)-3-{4-[2-(2-diethylaminomethyl-morpholin-4-yl)-ethoxy]-naphthalen-1-yl}-urea;

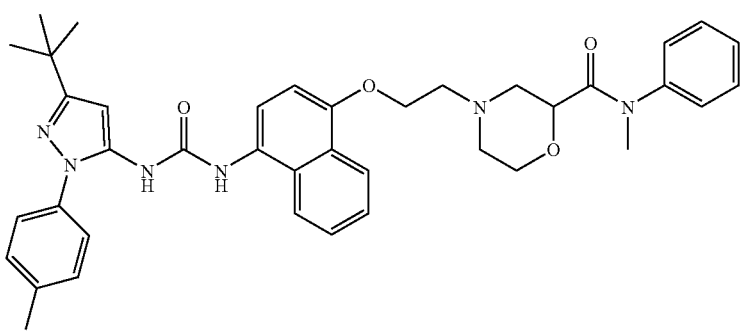 4-(2-{4-[3-(5-tert-Butyl-2-p-tolyl-2H-pyrazol-3-yl)-ureido]-naphthalen-1-yloxy}-ethyl)-morpholine-2-carboxylic acid methyl-phenyl-amide;

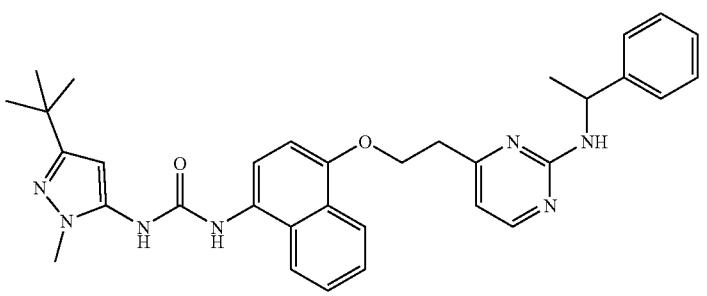 1-(5-tert-Butyl-2-methyl-2H-pyrazol-3-yl)-3-(4-{2-[2-(1-phenyl-ethylamino)-pyrimidin-4-yl]-ethoxy}-naphthalen-1-yl)-urea;

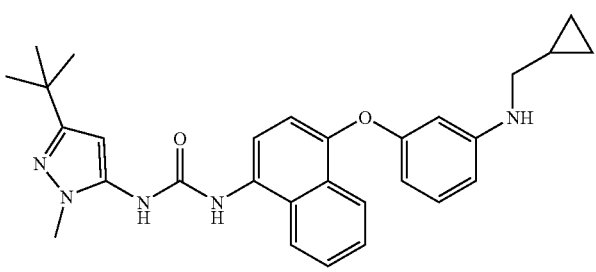 1-(5-tert-Butyl-2-methyl-2H-pyrazol-3-yl)-3-{4-[2-(cyclopropylmethyl-amino)-pyrimidin-4-yloxy]-naphthalen-1-yl}-urea;

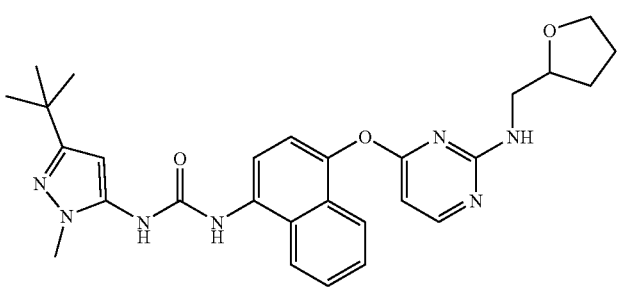 1-(5-tert-Butyl-2-methyl-2H-pyrazol-3-yl)-3-(4-{2-[(tetrahydro-furan-2-ylmethyl)-amino]-pyrimidin-4-yloxy}-naphthalen-1-yl)-urea;

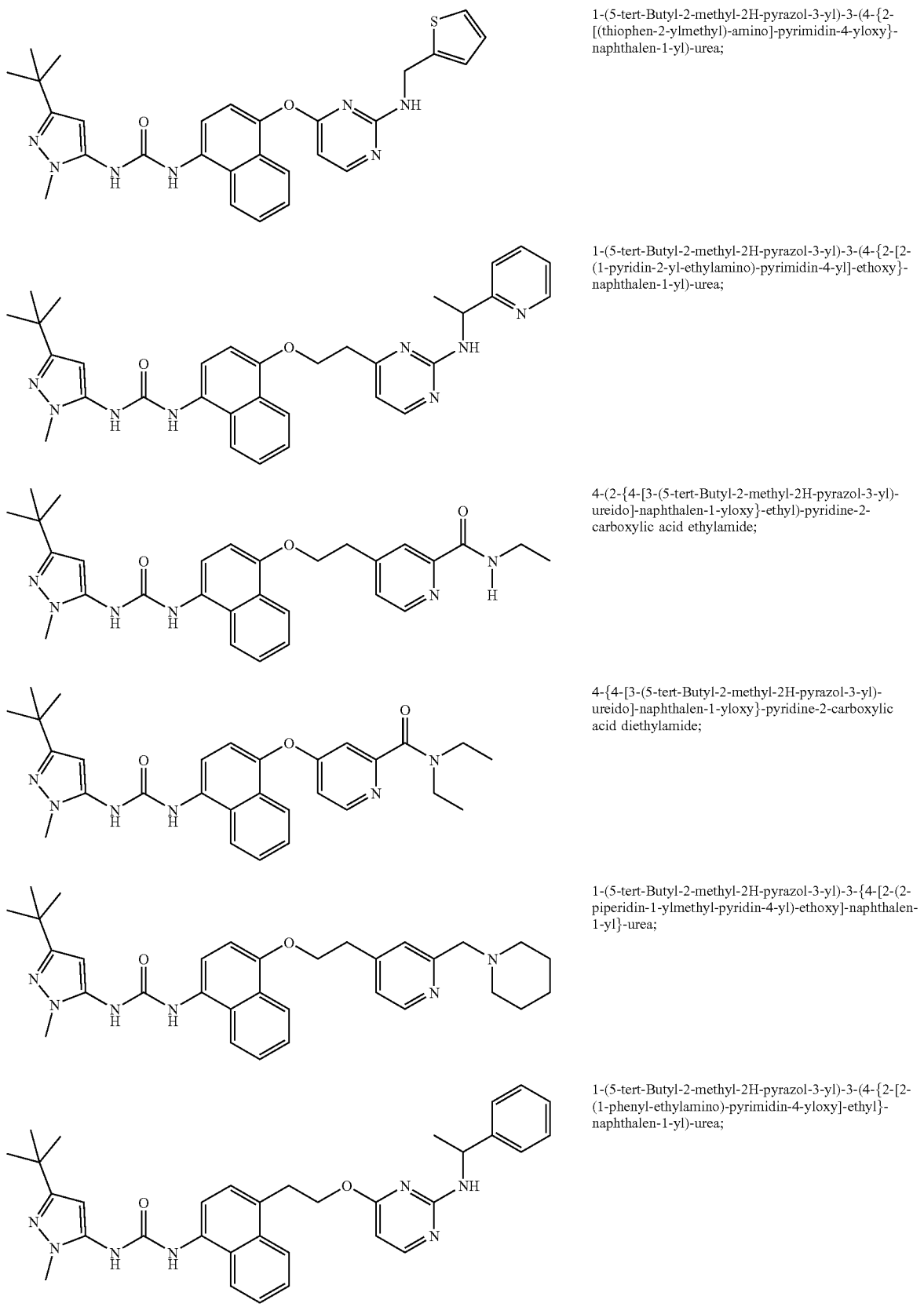

1-(5-tert-Butyl-2-methyl-2H-pyrazol-3-yl)-3-(4-{2-[(thiophen-2-ylmethyl)-amino]-pyrimidin-4-yloxy}-naphthalen-1-yl)-urea;

1-(5-tert-Butyl-2-methyl-2H-pyrazol-3-yl)-3-(4-{2-[2-(1-pyridin-2-yl-ethylamino)-pyrimidin-4-yl]-ethoxy}-naphthalen-1-yl)-urea;

4-(2-{4-[3-(5-tert-Butyl-2-methyl-2H-pyrazol-3-yl)-ureido]-naphthalen-1-yloxy}-ethyl)-pyridine-2-carboxylic acid ethylamide;

4-{4-[3-(5-tert-Butyl-2-methyl-2H-pyrazol-3-yl)-ureido]-naphthalen-1-yloxy}-pyridine-2-carboxylic acid diethylamide;

1-(5-tert-Butyl-2-methyl-2H-pyrazol-3-yl)-3-{4-[2-(2-piperidin-1-ylmethyl-pyridin-4-yl)-ethoxy]-naphthalen-1-yl}-urea;

1-(5-tert-Butyl-2-methyl-2H-pyrazol-3-yl)-3-(4-{2-[2-(1-phenyl-ethylamino)-pyrimidin-4-yloxy]-ethyl}-naphthalen-1-yl)-urea;

-continued

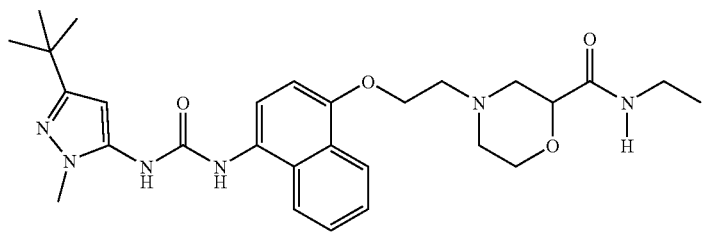
4-(2-{4-[3-(5-tert-Butyl-2-methyl-2H-pyrazol-3-yl)-ureido]-naphthalen-1-yloxy}-ethyl)-morpholine-2-carboxylic acid ethylamide;

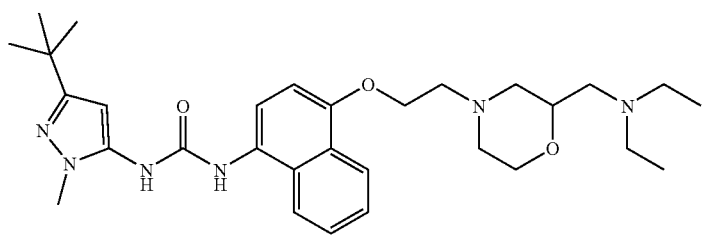
1-(5-tert-Butyl-2-methyl-2H-pyrazol-3-yl)-3-{4-[2-(2-diethylaminomethyl-morpholin-4-yl)-ethoxy]-naphthalen-1-yl}-urea;

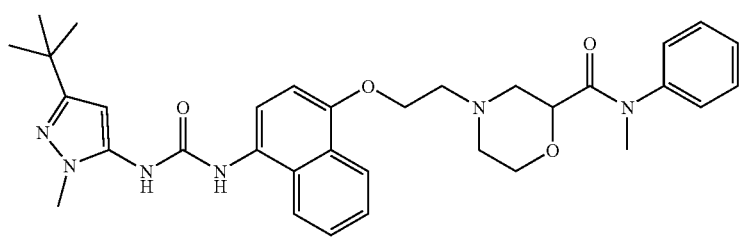
4-(2-{4-[3-(5-tert-Butyl-2-methyl-2H-pyrazol-3-yl)-ureido]-naphthalen-1-yloxy}-ethyl)-morpholine-2-carboxylic acid methyl-phenyl-amide;

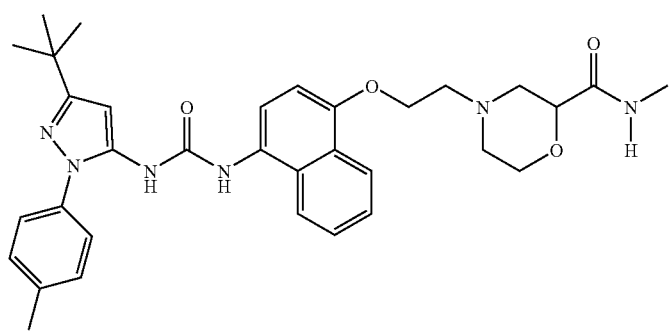
4-(2-{4-[3-(5-tert-Butyl-2-p-tolyl-2H-pyrazol-3-yl)-ureido]-naphthalen-1-yloxy}-ethyl)-morpholine-2-carboxylic acid methylamide;

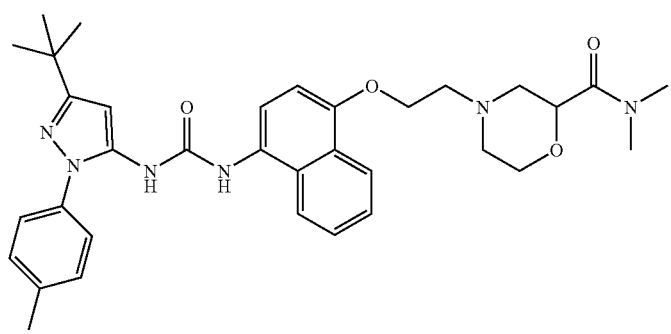
4-(2-{4-[3-(5-tert-Butyl-2-p-tolyl-2H-pyrazol-3-yl)-ureido]-naphthalen-1-yloxy}-ethyl)-morpholine-2-carboxylic acid dimethylamide;

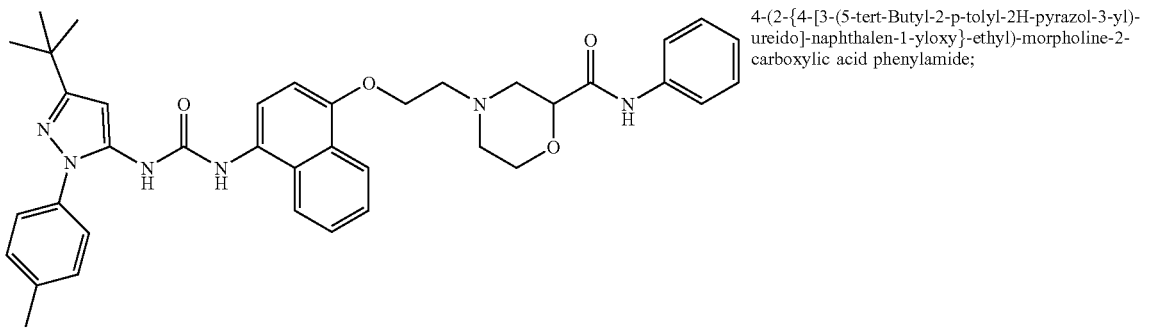
4-(2-{4-[3-(5-tert-Butyl-2-p-tolyl-2H-pyrazol-3-yl)-ureido]-naphthalen-1-yloxy}-ethyl)-morpholine-2-carboxylic acid phenylamide;
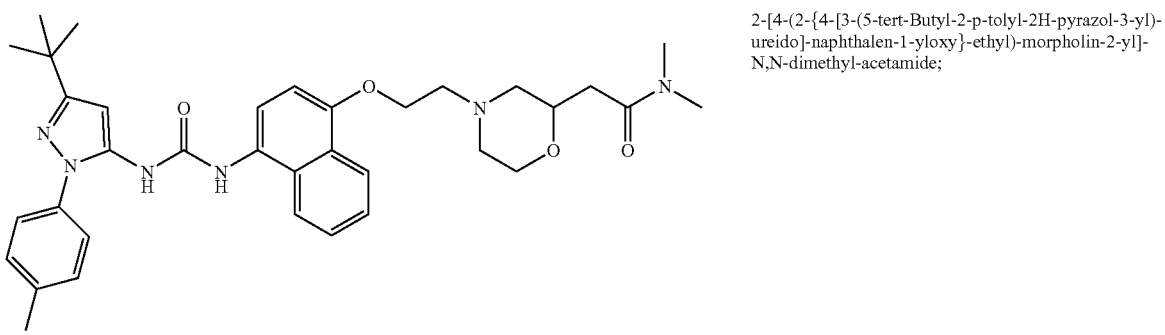
2-[4-(2-{4-[3-(5-tert-Butyl-2-p-tolyl-2H-pyrazol-3-yl)-ureido]-naphthalen-1-yloxy}-ethyl)-morpholin-2-yl]-N,N-dimethyl-acetamide;
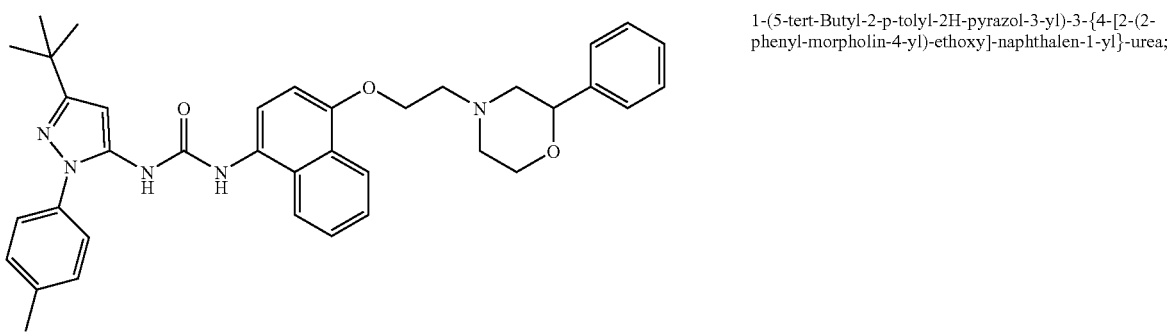
1-(5-tert-Butyl-2-p-tolyl-2H-pyrazol-3-yl)-3-{4-[2-(2-phenyl-morpholin-4-yl)-ethoxy]-naphthalen-1-yl}-urea;
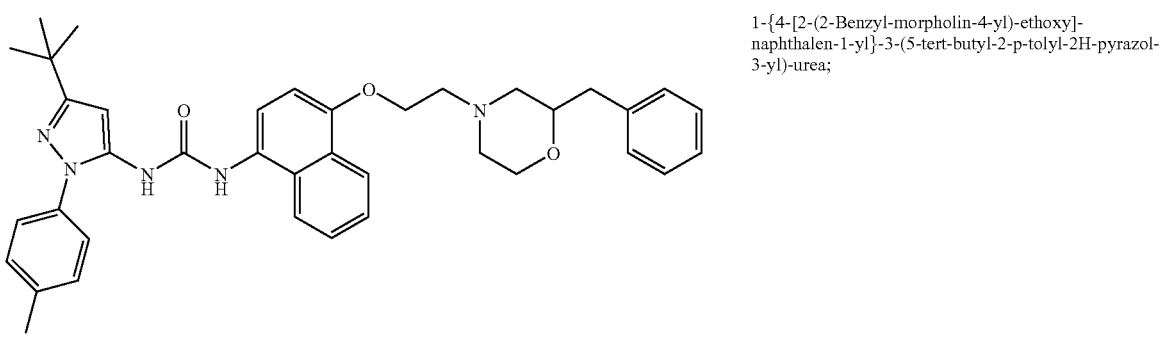
1-{4-[2-(2-Benzyl-morpholin-4-yl)-ethoxy]-naphthalen-1-yl}-3-(5-tert-butyl-2-p-tolyl-2H-pyrazol-3-yl)-urea;

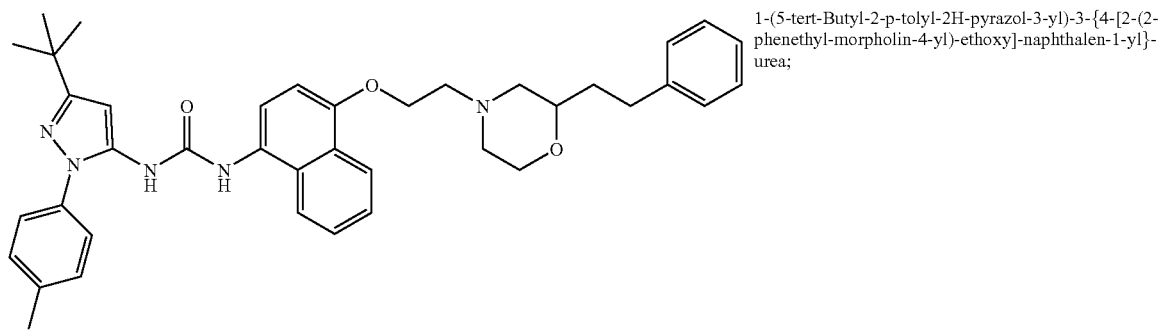
1-(5-tert-Butyl-2-p-tolyl-2H-pyrazol-3-yl)-3-{4-[2-(2-phenethyl-morpholin-4-yl)-ethoxy]-naphthalen-1-yl}-urea;
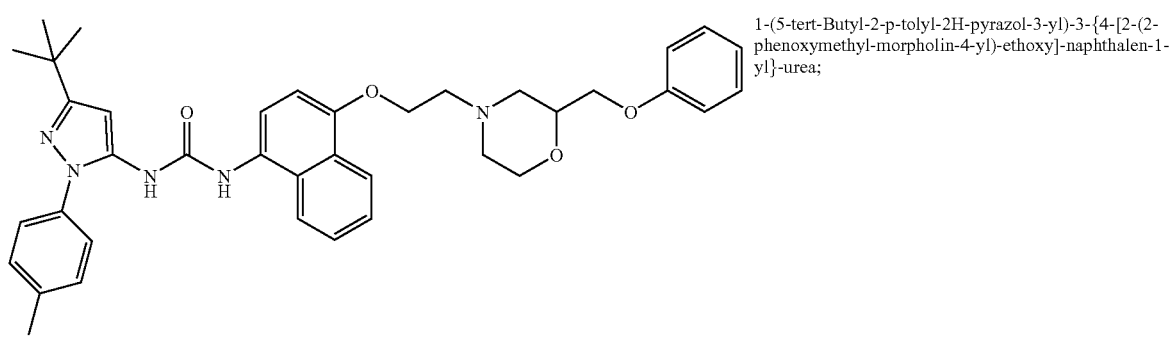
1-(5-tert-Butyl-2-p-tolyl-2H-pyrazol-3-yl)-3-{4-[2-(2-phenoxymethyl-morpholin-4-yl)-ethoxy]-naphthalen-1-yl}-urea;
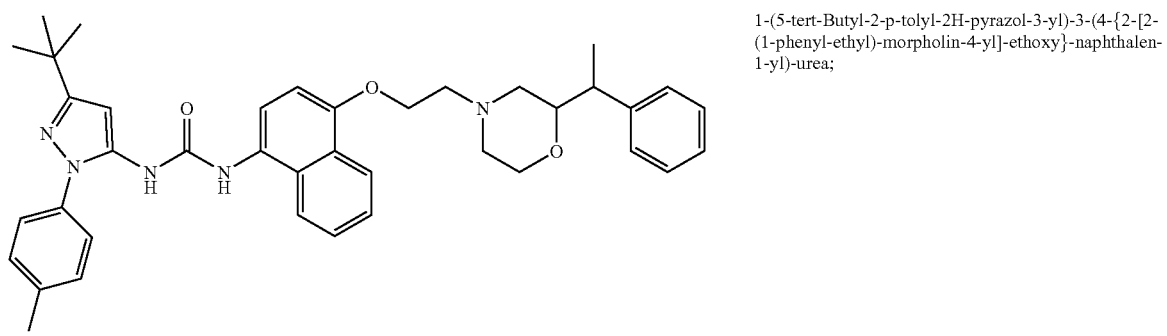
1-(5-tert-Butyl-2-p-tolyl-2H-pyrazol-3-yl)-3-(4-{2-[2-(1-phenyl-ethyl)-morpholin-4-yl]-ethoxy}-naphthalen-1-yl)-urea;
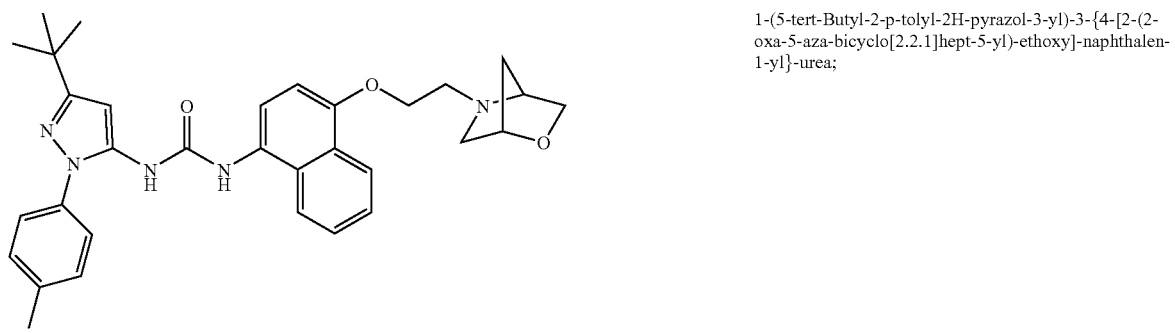
1-(5-tert-Butyl-2-p-tolyl-2H-pyrazol-3-yl)-3-{4-[2-(2-oxa-5-aza-bicyclo[2.2.1]hept-5-yl)-ethoxy]-naphthalen-1-yl}-urea;

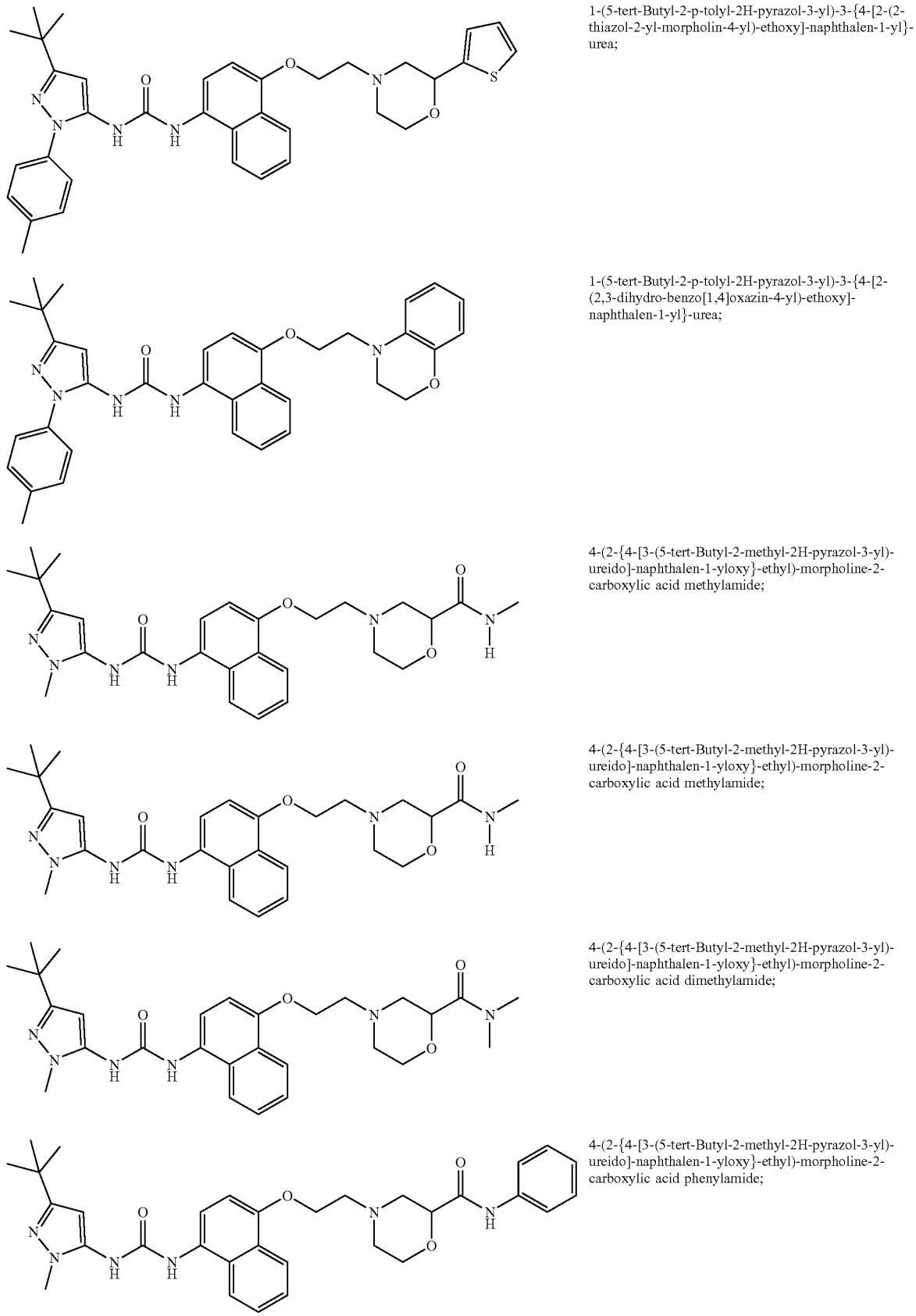

1-(5-tert-Butyl-2-p-tolyl-2H-pyrazol-3-yl)-3-{4-[2-(2-thiazol-2-yl-morpholin-4-yl)-ethoxy]-naphthalen-1-yl}-urea;

1-(5-tert-Butyl-2-p-tolyl-2H-pyrazol-3-yl)-3-{4-[2-(2,3-dihydro-benzo[1,4]oxazin-4-yl)-ethoxy]-naphthalen-1-yl}-urea;

4-(2-{4-[3-(5-tert-Butyl-2-methyl-2H-pyrazol-3-yl)-ureido]-naphthalen-1-yloxy}-ethyl)-morpholine-2-carboxylic acid methylamide;

4-(2-{4-[3-(5-tert-Butyl-2-methyl-2H-pyrazol-3-yl)-ureido]-naphthalen-1-yloxy}-ethyl)-morpholine-2-carboxylic acid methylamide;

4-(2-{4-[3-(5-tert-Butyl-2-methyl-2H-pyrazol-3-yl)-ureido]-naphthalen-1-yloxy}-ethyl)-morpholine-2-carboxylic acid dimethylamide;

4-(2-{4-[3-(5-tert-Butyl-2-methyl-2H-pyrazol-3-yl)-ureido]-naphthalen-1-yloxy}-ethyl)-morpholine-2-carboxylic acid phenylamide;

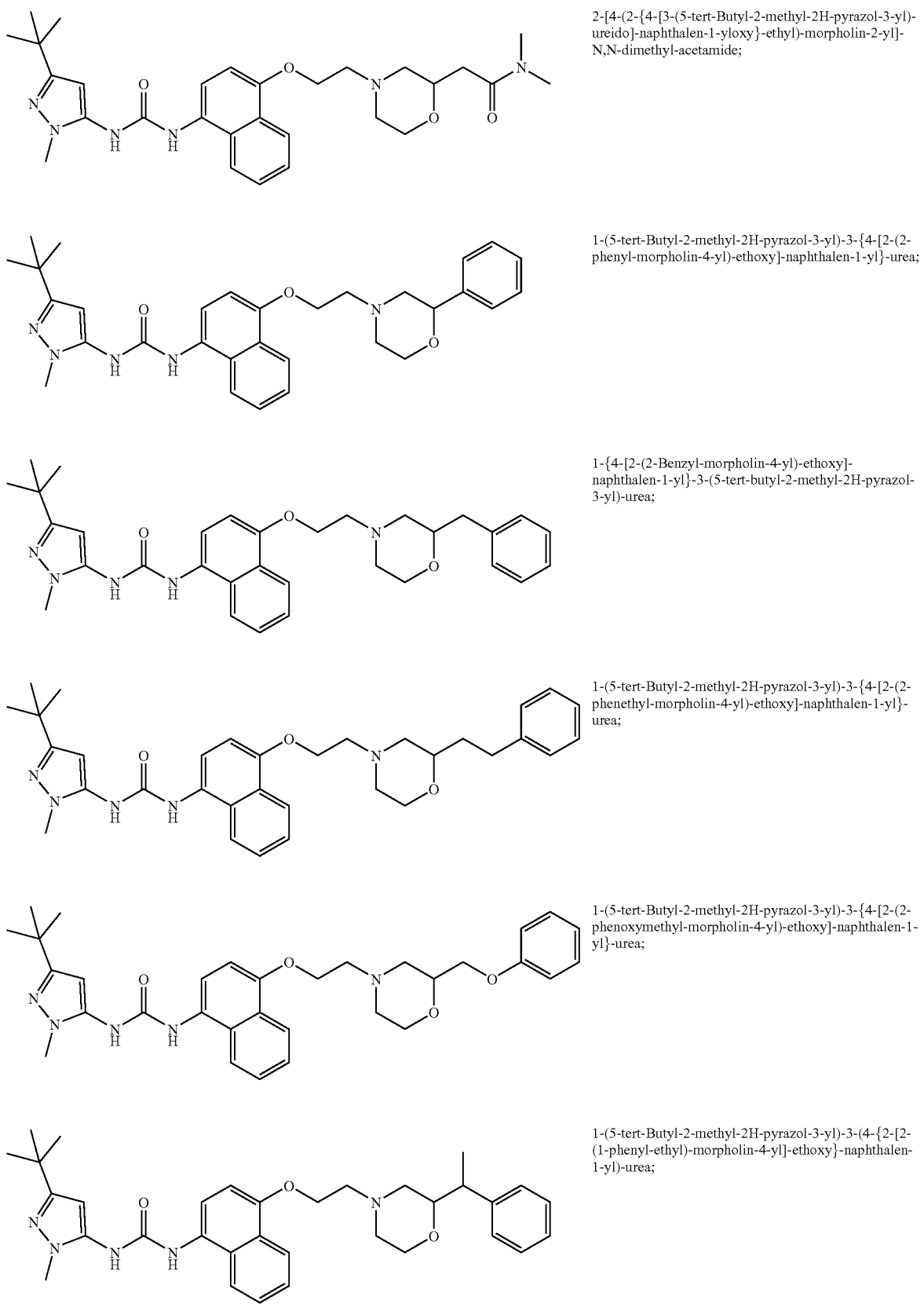

2-[4-(2-{4-[3-(5-tert-Butyl-2-methyl-2H-pyrazol-3-yl)-ureido]-naphthalen-1-yloxy}-ethyl)-morpholin-2-yl]-N,N-dimethyl-acetamide;

1-(5-tert-Butyl-2-methyl-2H-pyrazol-3-yl)-3-{4-[2-(2-phenyl-morpholin-4-yl)-ethoxy]-naphthalen-1-yl}-urea;

1-{4-[2-(2-Benzyl-morpholin-4-yl)-ethoxy]-naphthalen-1-yl}-3-(5-tert-butyl-2-methyl-2H-pyrazol-3-yl)-urea;

1-(5-tert-Butyl-2-methyl-2H-pyrazol-3-yl)-3-{4-[2-(2-phenethyl-morpholin-4-yl)-ethoxy]-naphthalen-1-yl}-urea;

1-(5-tert-Butyl-2-methyl-2H-pyrazol-3-yl)-3-{4-[2-(2-phenoxymethyl-morpholin-4-yl)-ethoxy]-naphthalen-1-yl}-urea;

1-(5-tert-Butyl-2-methyl-2H-pyrazol-3-yl)-3-(4-{2-[2-(1-phenyl-ethyl)-morpholin-4-yl]-ethoxy}-naphthalen-1-yl)-urea;

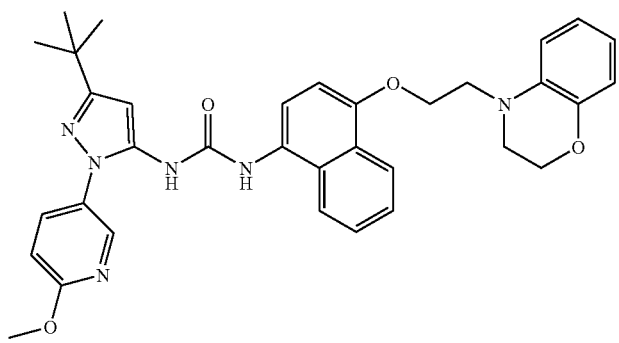

1-(5-tert-Butyl-2-(6-methoxy-pyridin-3-yl)-2H-pyrazol-3-yl)-3-{4-[2-(2,3-dihydro-benzo[1,4]oxazin-4-yl)-ethoxy]-naphthalen-1-yl}-urea;

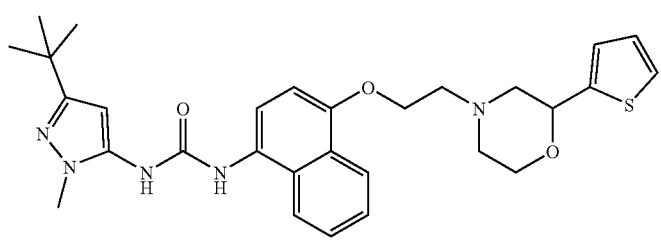

1-(5-tert-Butyl-2-methyl-2H-pyrazol-3-yl)-3-{4-[2-(2-thiazol-2-yl-morpholin-4-yl)-ethoxy]-naphthalen-1-yl}-urea;

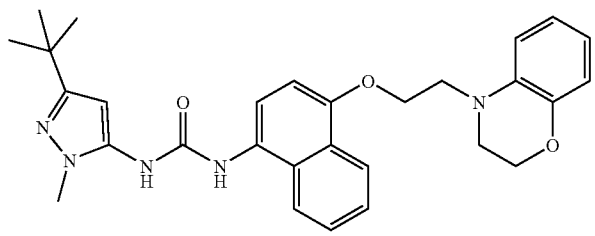

1-(5-tert-Butyl-2-methyl-2H-pyrazol-3-yl)-3-{4-[2-(2,3-dihydro-benzo[1,4]oxazin-4-yl)-ethoxy]-naphthalen-1-yl}-urea;

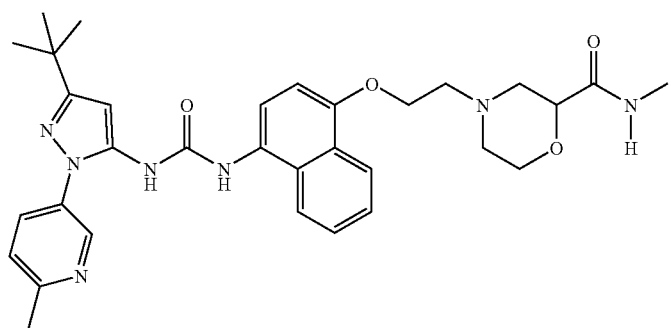

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methylamide;

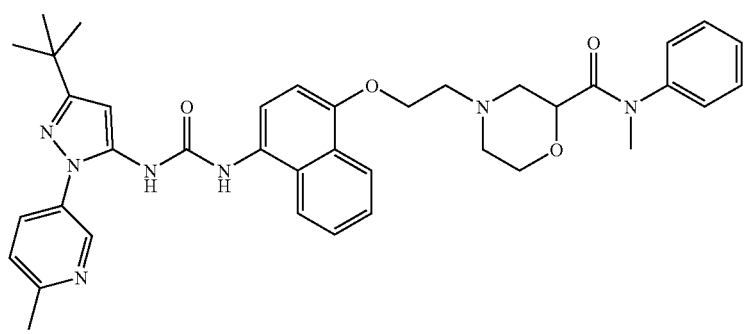

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methyl-phenyl-amide;

-continued

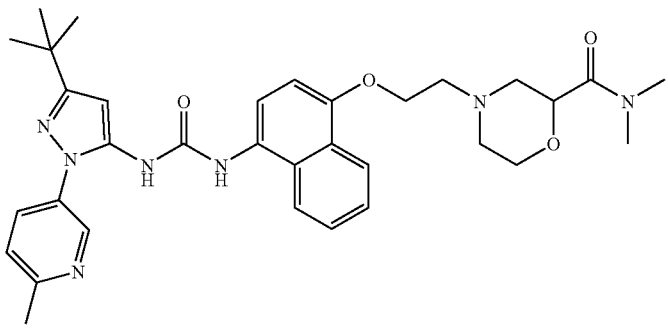

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid dimethylamide;

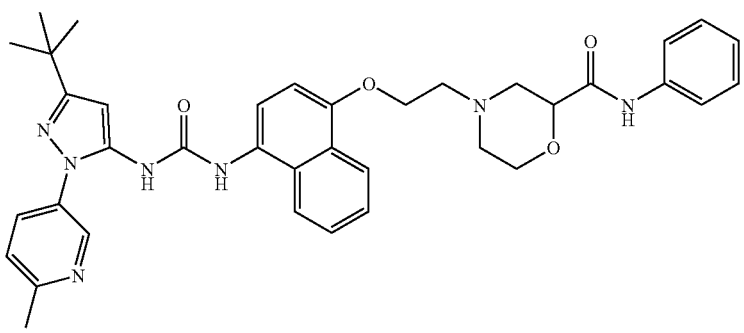

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid phenylamide;

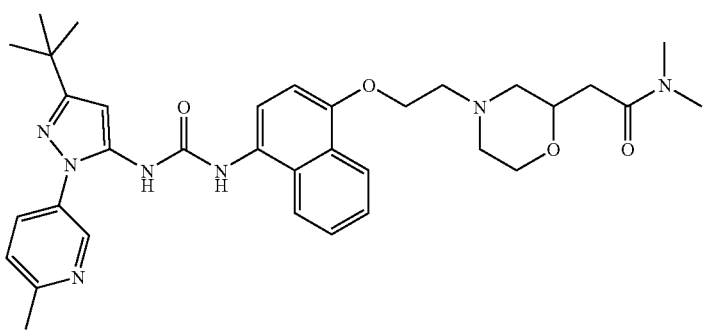

2-{4-[2-(4-{3-[5-tert-Butyl-2-(6-methyl-pyridin-3-yl)-2H-pyrazol-3-yl]-ureido}-naphthalen-1-yloxy)-ethyl]-morpholin-2-yl}-N,N-dimethyl-acetamide;

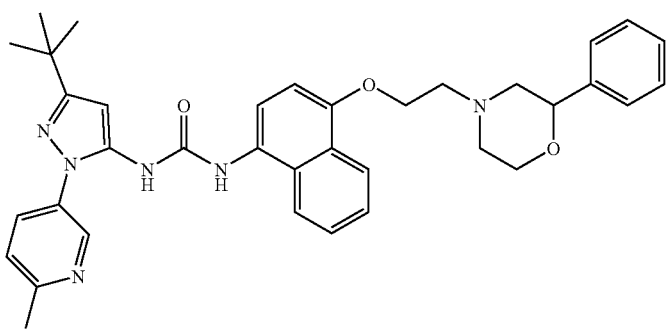

1-[5-tert-Butyl-2-(6-methyl-pyridin-3-yl)-2H-pyrazol-3-yl]-3-{4-[2-(2-phenyl-morpholin-4-yl)-ethoxy]-naphthalen-1-yl}-urea;

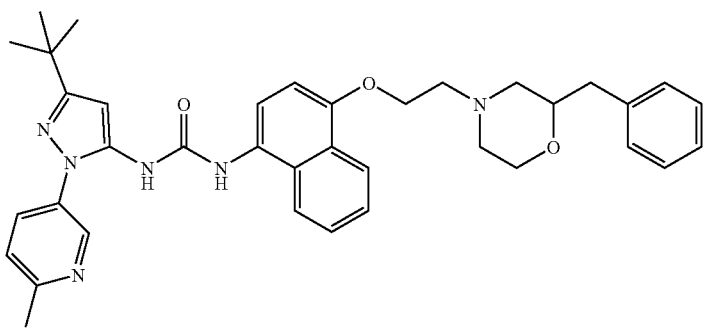

1-{4-[2-(2-Benzyl-morpholin-4-yl)-ethoxy]-naphthalen-1-yl}-3-[5-tert-butyl-2-(6-methyl-pyridin-3-yl)-2H-pyrazol-3-yl]-urea;

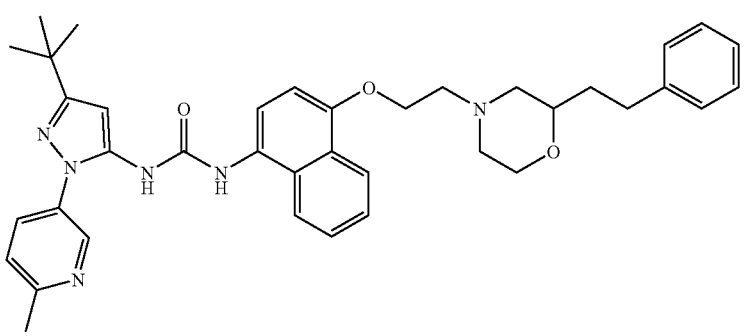

1-[5-tert-Butyl-2-(6-methyl-pyridin-3-yl)-2H-pyrazol-3-yl]-3-{4-[2-(2-phenethyl-morpholin-4-yl)-ethoxy]-naphthalen-1-yl}-urea;

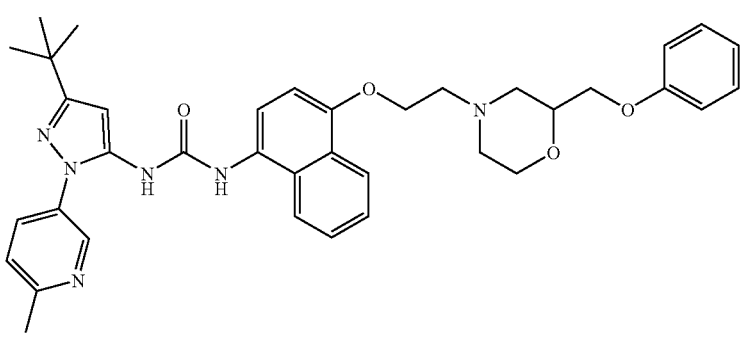

1-[5-tert-Butyl-2-(6-methyl-pyridin-3-yl)-2H-pyrazol-3-yl]-3-{4-[2-(2-phenoxymethyl-morpholin-4-yl)-ethoxy]-naphthalen-1-yl}-urea;

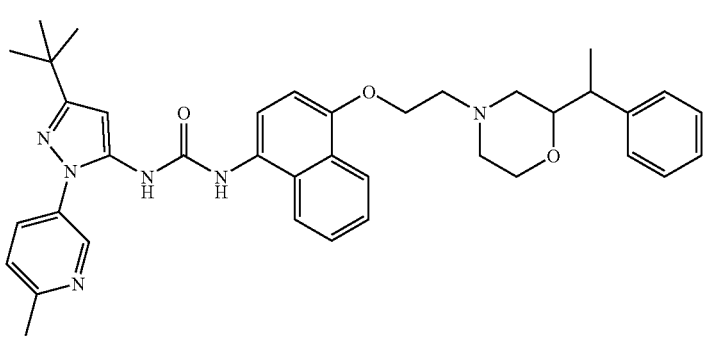

1-[5-tert-Butyl-2-(6-methyl-pyridin-3-yl)-2H-pyrazol-3-yl]-3-(4-{2-[2-(1-phenyl-ethyl)-morpholin-4-yl]-ethoxy}-naphthalen-1-yl)-urea;

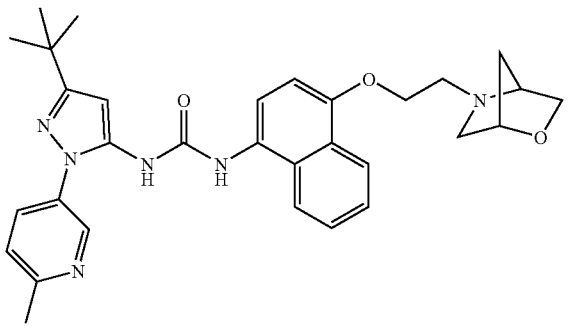

1-[5-tert-Butyl-2-(6-methyl-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;

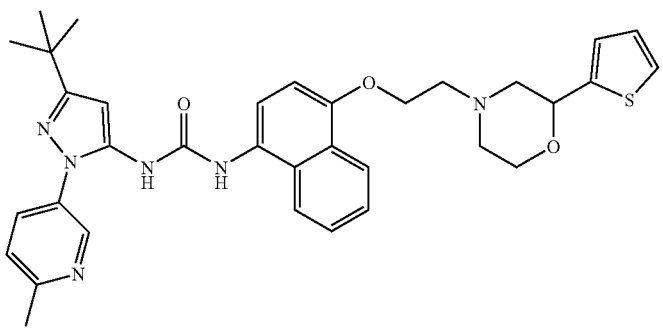

1-[5-tert-Butyl-2-(6-methyl-pyridin-3-yl)-2H-pyrazol-3-yl]-3-{4-[2-(2-thiazol-2-yl-morpholin-4-yl)-ethoxy]-naphthalen-1-yl}-urea;

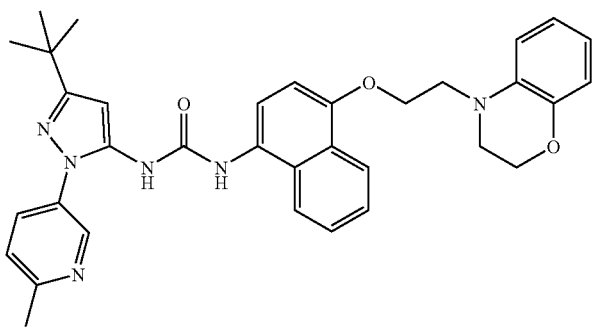

1-[5-tert-Butyl-2-(6-methyl-pyridin-3-yl)-2H-pyrazol-3-yl]-3-{4-[2-(2,3-dihydro-benzo[1,4]oxazin-4-yl)-ethoxy]-naphthalen-1-yl}-urea;

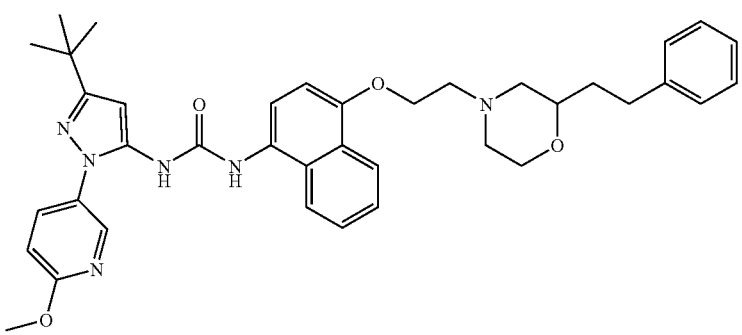

1-[5-tert-Butyl-2-(6-methoxy-pyridin-3-yl)-2H-pyrazol-3-yl]-3-{4-[2-(2-phenethyl-morpholin-4-yl)-ethoxy]-naphthalen-1-yl}-urea;

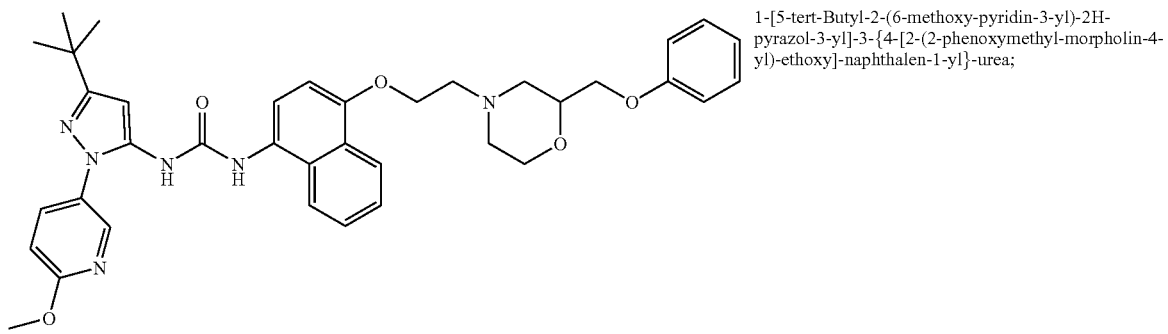

1-[5-tert-Butyl-2-(6-methoxy-pyridin-3-yl)-2H-pyrazol-3-yl]-3-{4-[2-(2-phenoxymethyl-morpholin-4-yl)-ethoxy]-naphthalen-1-yl}-urea;

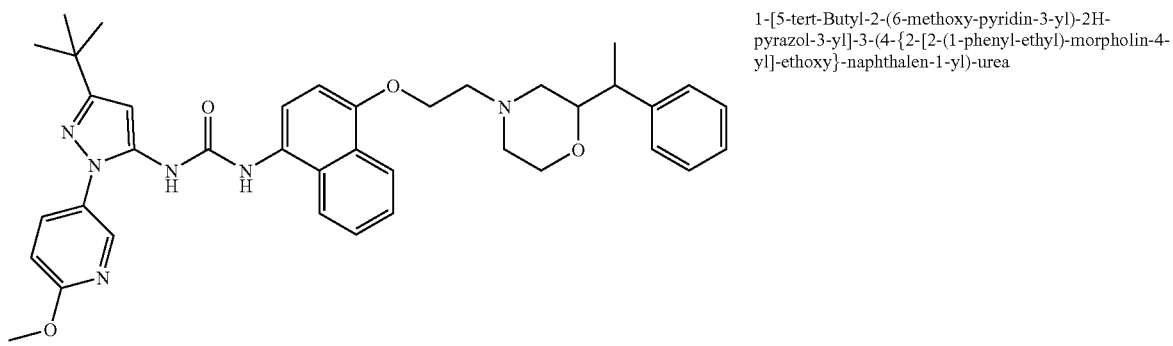

1-[5-tert-Butyl-2-(6-methoxy-pyridin-3-yl)-2H-pyrazol-3-yl]-3-(4-{2-[2-(1-phenyl-ethyl)-morpholin-4-yl]-ethoxy}-naphthalen-1-yl)-urea

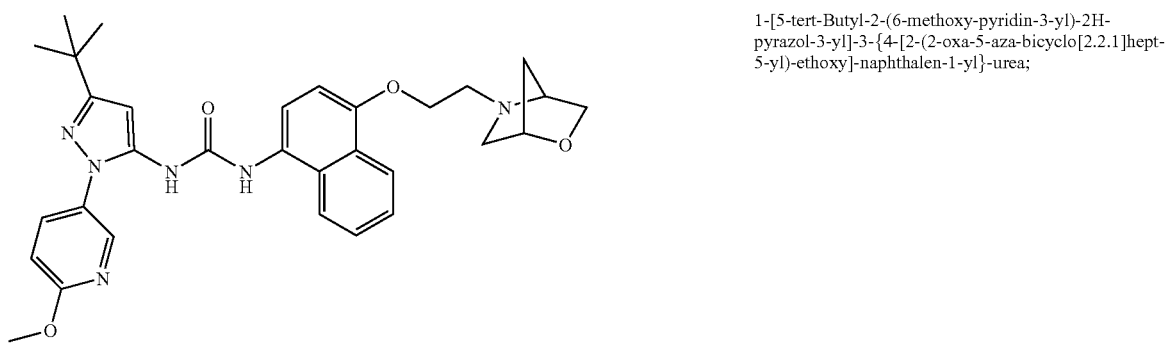

1-[5-tert-Butyl-2-(6-methoxy-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;

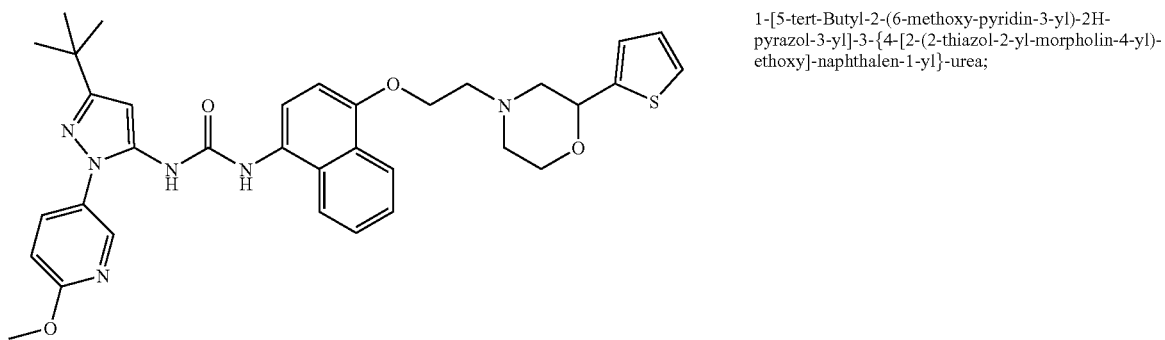

1-[5-tert-Butyl-2-(6-methoxy-pyridin-3-yl)-2H-pyrazol-3-yl]-3-{4-[2-(2-thiazol-2-yl-morpholin-4-yl)-ethoxy]-naphthalen-1-yl}-urea;

-continued

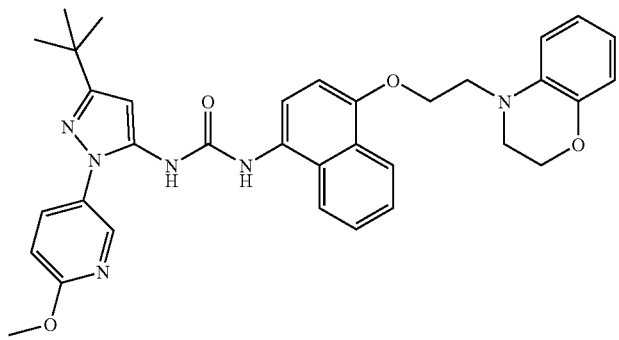

1-[5-tert-Butyl-2-(6-methoxy-pyridin-3-yl)-2H-pyrazol-3-yl]-3-{4-[2-(2,3-dihydro-benzo[1,4]oxazin-4-yl)-ethoxy]-naphthalen-1-yl}-urea;

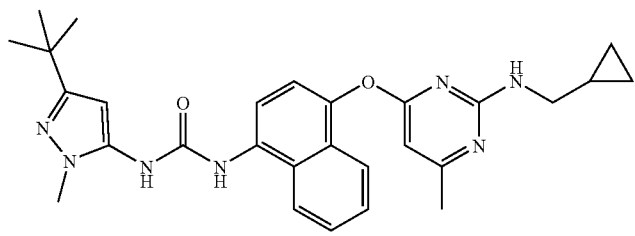

1-(5-tert-Butyl-2-methyl-2H-pyrazol-3-yl)-3-{4-[2-(cyclopropylmethyl-amino)-6-methyl-pyrimidin-4-yloxy]-naphthalen-1-yl}-urea;

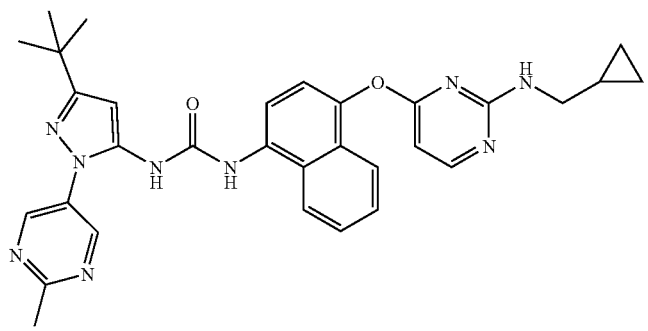

1-(5-tert-Butyl-2-{2-methyl-pyrimidin-5-yl)-3-{4-[2-(cyclopropylmethyl-amino)-pyrimidin-4-yloxy]-ethyl}-naphthalen-1-yl)-urea and

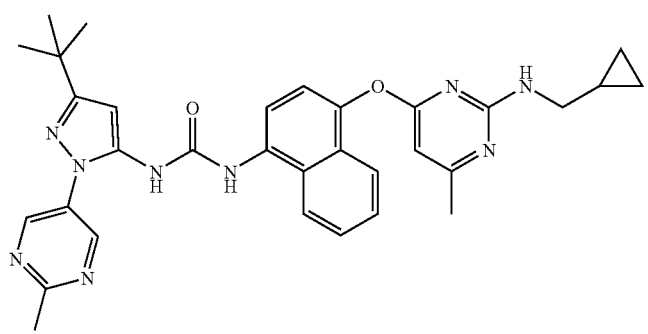

1-(5-tert-Butyl-2-{2-methyl-pyrimidin-5-yl)-3-{4-[2-(cyclopropylmethyl-amino)-6-methyl-pyrimidin-4-yloxy]-ethyl}-naphthalen-1-yl)-urea or the pharmaceutically acceptable acids or salts thereof.

The following are preferred compounds of the invention

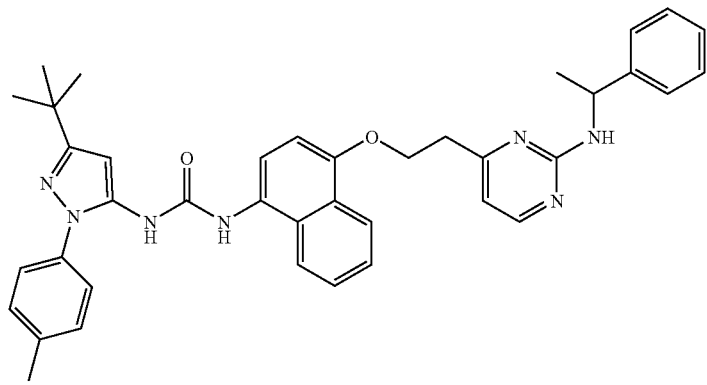

1-(5-tert-Butyl-2-p-tolyl-2H-pyrazol-3-yl)-3-(4-{2-[2-(1-phenyl-ethylamino)-pyrimidin-4-yl]-ethoxy}-naphthalen-1-yl)-urea;

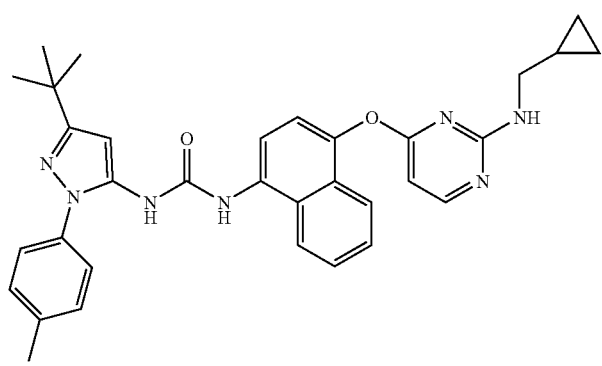

1-(5-tert-Butyl-2-p-tolyl-2H-pyrazol-3-yl)-3-{4-[2-(cyclopropylmethyl-amino)-pyrimidin-4-yloxy]-naphthalen-1-yl}-urea;

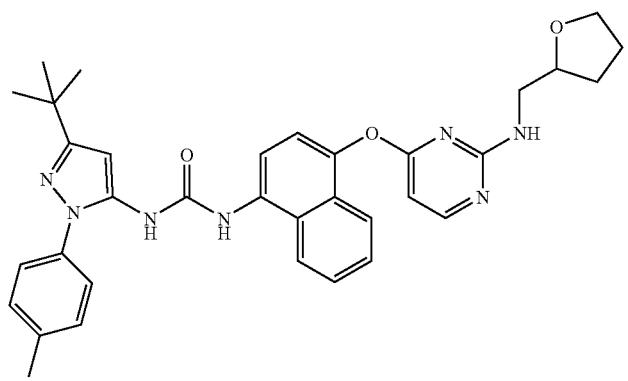

1-(5-tert-Butyl-2-p-tolyl-2H-pyrazol-3-yl)-3-(4-{2-[(tetrahydro-furan-2-ylmethyl)-amino]-pyrimidin-4-yloxy}-naphthalen-1-yl)-urea;

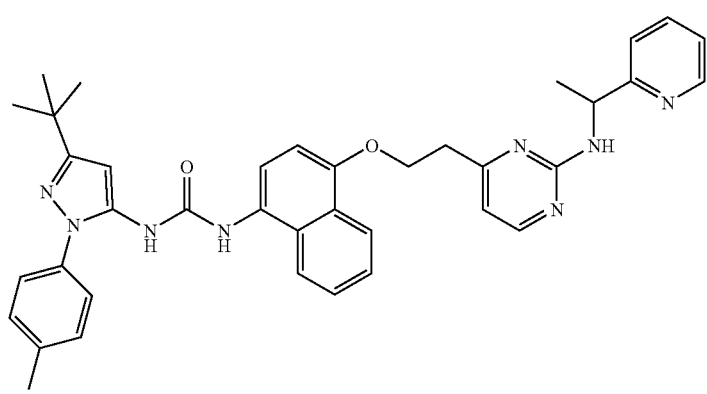

1-(5-tert-Butyl-2-p-tolyl-2H-pyrazol-3-yl)-3-(4-{2-[2-(1-pyridin-2-yl-ethylamino)-pyrimidin-4-yl]-ethoxy}-naphthalen-1-yl)-urea;

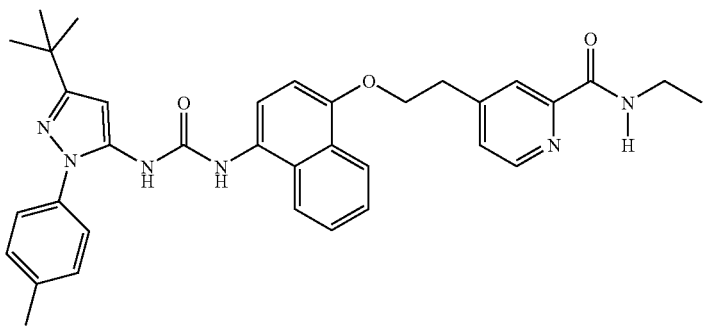

4-(2-{4-[3-(5-tert-Butyl-2-p-tolyl-2H-pyrazol-3-yl)-ureido]-naphthalen-1-yloxy}-ethyl)-pyridine-2-carboxylic acid ethylamide;

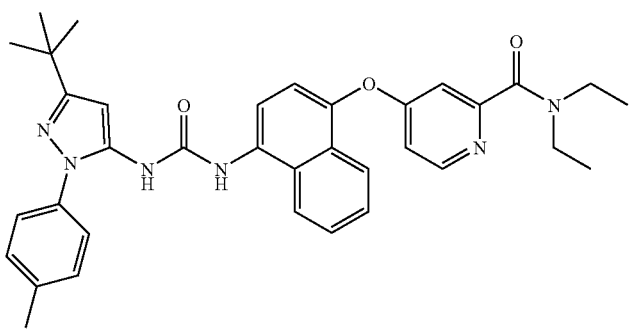

4-{4-[3-(5-tert-Butyl-2-p-tolyl-2H-pyrazol-3-yl)-ureido]-naphthalen-1-yloxy}-pyridine-2-carboxylic acid diethylamide;

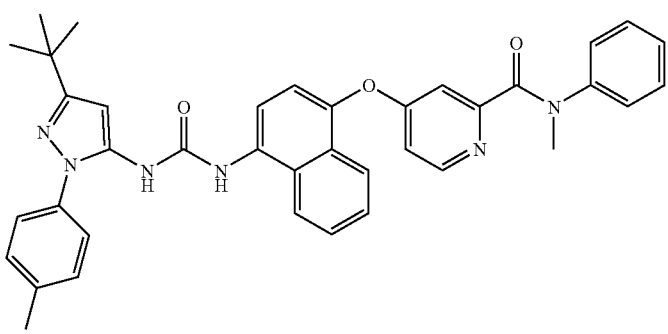

4-(4-{3-[5-tert-Butyl-2-(6-methyl-pyridin-3-yl)-2H-pyrazol-3-yl]-ureido}-naphthalen-1-yloxy)-pyridine-2-carboxylic acid methyl-phenyl-amide;

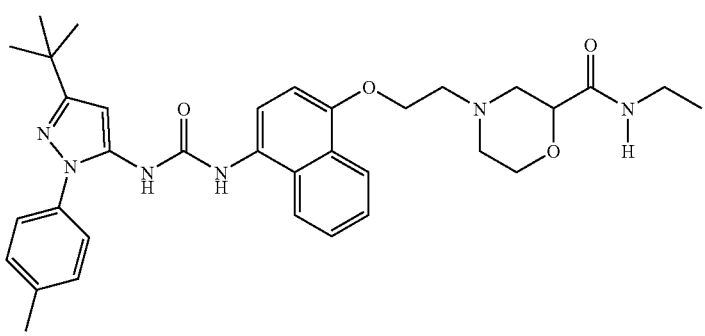

4-(2-{4-[3-(5-tert-Butyl-2-p-tolyl-2H-pyrazol-3-yl)-ureido]-naphthalen-1-yloxy}-ethyl)-morpholine-2-carboxylic acid ethylamide;

-continued

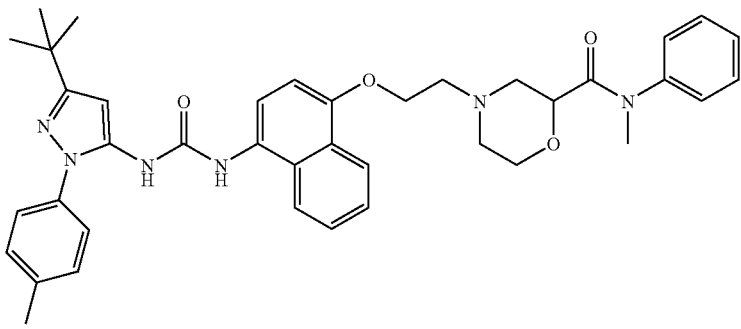

4-(2-{4-[3-(5-tert-Butyl-2-p-tolyl-2H-pyrazol-3-yl)-ureido]-naphthalen-1-yloxy}-ethyl)-morpholine-2-carboxylic acid methyl-phenyl-amide;

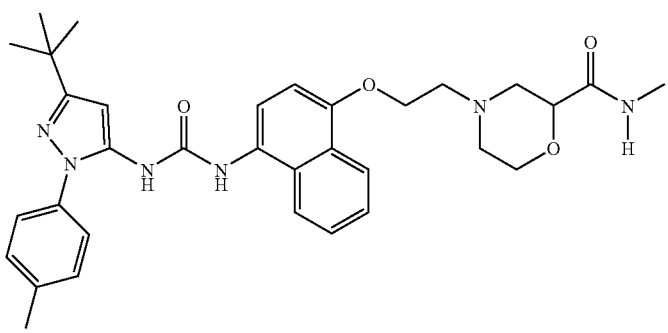

4-(2-{4-[3-(5-tert-Butyl-2-p-tolyl-2H-pyrazol-3-yl)-ureido]-naphthalen-1-yloxy}-ethyl)-morpholine-2-carboxylic acid methylamide;

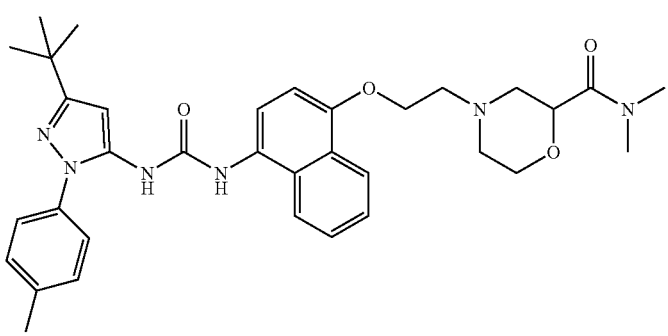

4-(2-{4-[3-(5-tert-Butyl-2-p-tolyl-2H-pyrazol-3-yl)-ureido]-naphthalen-1-yloxy}-ethyl)-morpholine-2-carboxylic acid dimethylamide;

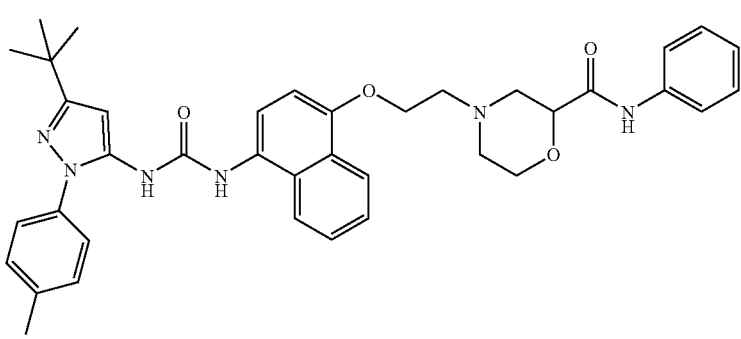

4-(2-{4-[3-(5-tert-Butyl-2-p-tolyl-2H-pyrazol-3-yl)-ureido]-naphthalen-1-yloxy}-ethyl)-morpholine-2-carboxylic acid phenylamide;

-continued

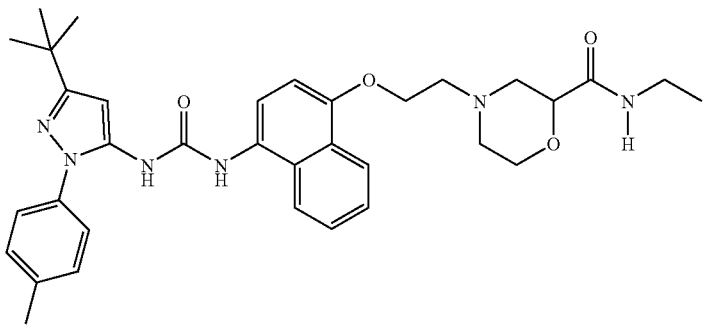

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methylamide;

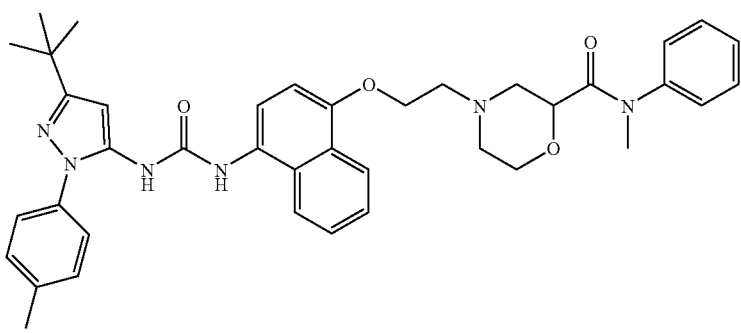

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methyl-phenyl-amide;

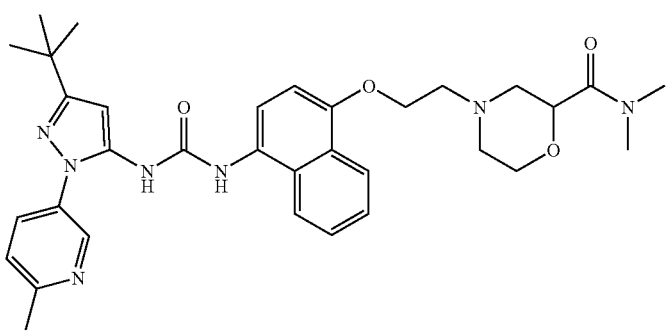

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid dimethylamide;

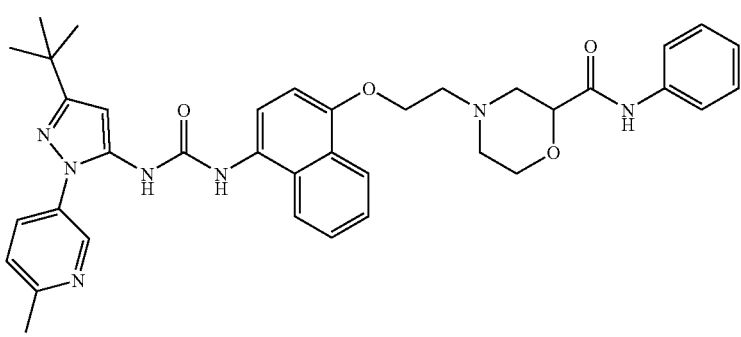

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid phenyl-amide;

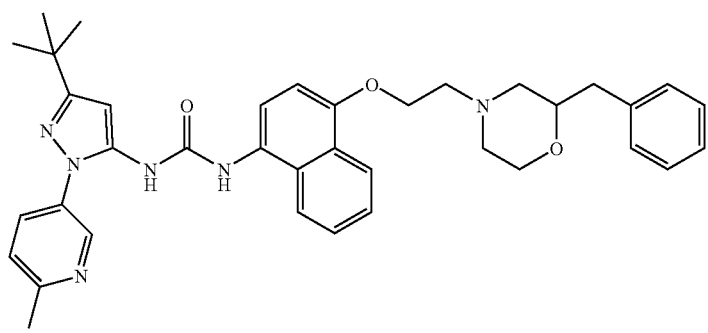

1-{4-[2-(2-Benzyl-morpholin-4-yl)-ethoxy]-naphthalen-1-yl}-3-[5-tert-butyl-2-(6-methyl-pyridin-3-yl)-2H-pyrazol-3-yl]-urea;

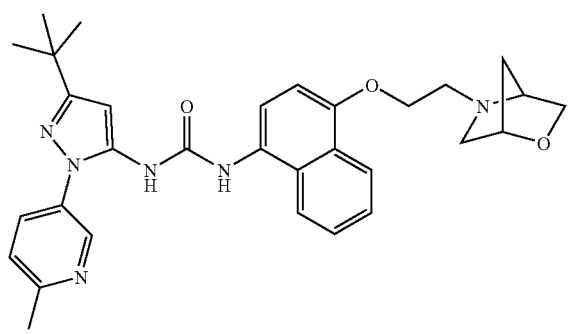

1-[5-tert-Butyl-2-(6-methyl-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;

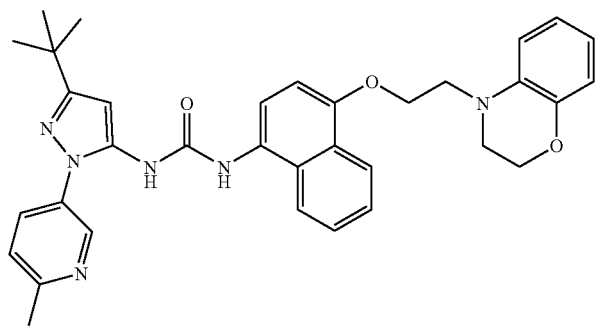

1-[5-tert-Butyl-2-(6-methyl-pyridin-3-yl)-2H-pyrazol-3-yl]-3-{4-[2-(2,3-dihydro-benzo[1,4]oxazin-4-yl)-ethoxy]-naphthalen-1-yl}-urea;

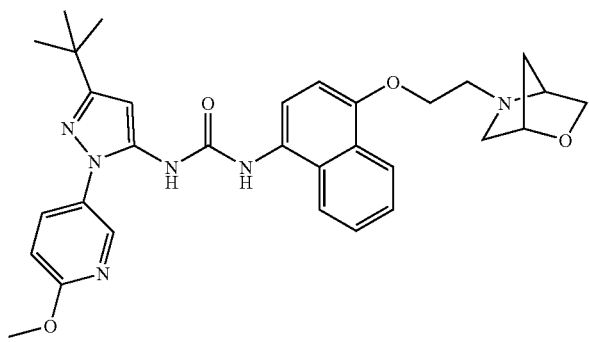

1-[5-tert-Butyl-2-(6-methoxy-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;

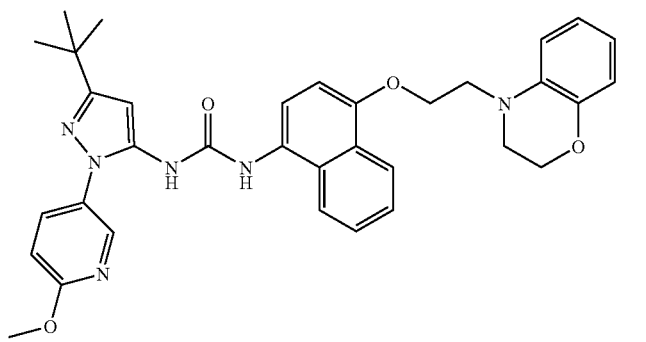

1-[5-tert-Butyl-2-(6-methoxy-pyridin-3-yl)-2H-pyrazol-3-yl]-3-{4-[2-(2,3-dihydro-benzo[1,4]oxazin-4-yl)-ethoxy]-naphthalen-1-yl}-urea;

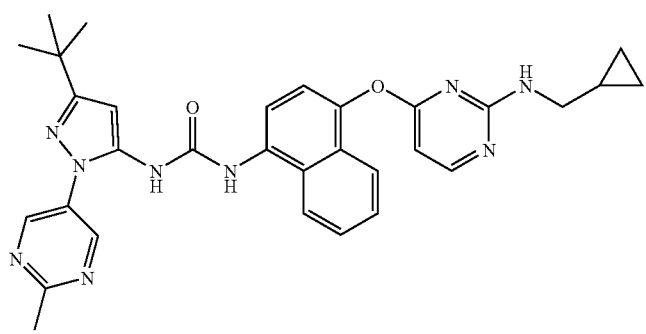

1-(5-tert-Butyl-2-{2-methyl-pyrimidin-5-yl)-3-{4-[2-(cyclopropylmethyl-amino)-pyrimidin-4-yloxy]-ethyl}-naphthalen-1-yl)-urea and

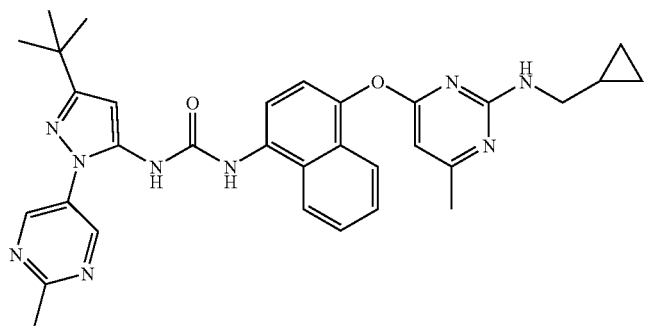

1-(5-tert-Butyl-2-{2-methyl-pyrimidin-5-yl)-3-{4-[2-(cyclopropylmethyl-amino)-6-methyl-pyrimidin-4-yloxy]-ethyl}-naphthalen-1-yl)-urea or the pharmaceutically acceptable acids or salts thereof.

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean a hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl or 2-oxa- or 2-thia-5-aza-bicyclo[2.2.1]heptanyl.

The term "heteroaryl" shall be understood to mean an aromatic 5–8 membered monocyclic or 8–11 membered bicyclic ring containing 1–4 heteroatoms such as N, O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4]oxazin-3-onyl, benzodioxolyl, benzo[1,3]dioxol-2-onyl, tetrahydrobenzopyranyl, indolyl, indolinyl, indolonyl, indolinonyl, phthalimidyl.

The term "heteroatom" as used herein shall be understood to mean atoms other than carbon such as O, N, S and P.

In all alkyl groups or carbon chains where one or more carbon atoms are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N-($C_1$–$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, toxic shock syndrome, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis.

The compounds are also useful in methods for treating: complications including restenosis following percutaneous transluminal coronary angioplasty, traumatic arthritis, sepsis, chronic obstructive pulmonary disease and congestive heart failure.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. provisional application No. 60/313,527, each incorporated by reference herein in their entirety.

Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Synthetic Methods

Compounds of Formula (I) may be prepared by methods described in U.S. Pat. No. 6,319,921, incorporated herein by reference and methods described below and known in the art. Intermediates used in the preparation of compounds of the invention are either commercially available or readily prepared by methods known to those skilled in the art. Further reference in this regard may be made to U.S. application Ser. Nos. 09/505,582, 09/484,638, 09/714,539, 09/611,109, 09/698,442 and U.S. provisional application Nos. 60/216,283, 60/283,642, 60/291,425, 60/293,600 and 60/295,909, each incorporated herein by reference in their entirety.

Optimum reaction conditions and reaction times may vary depending on the particular reactants used. Unless otherwise specified, solvents, temperatures, pressures, and other reaction conditions may be readily selected by one of ordinary skill in the art. Typically, reaction progress may be monitored by thin layer chromatography (TLC), if desired, and intermediates and products may be purified by chromatography on silica gel and/or by recrystallization.

The substituted morpholine intermediates used in the preparation of compounds of Formula (I) are readily prepared by methods known in the art or are available commercially as indicated in Table 1 below.

TABLE 1

| Morpholine Intermediate | Reference |
| --- | --- |
| 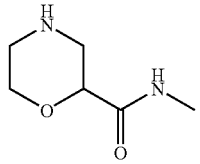 | WO 01/34150<br>WO 00/09491 |
| 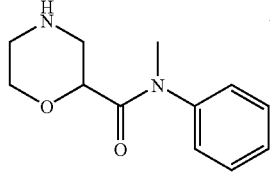 | WO 01/34150<br>WO 00/09491 |
| 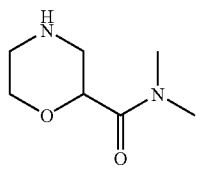 | WO 01/34150<br>WO 00/09491 |
| 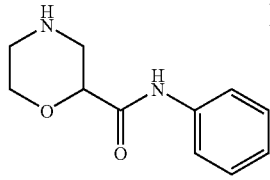 | WO 01/34150<br>WO 00/09491 |

TABLE 1-continued

| Morpholine Intermediate | Reference |
|---|---|
| | D. J. Blythin et al., Biorog. Med. Chem Letters 6 1529 (1996) |
| | T. Bailey et al., J. Het. Chem., 6 751 (1969) |
| | G. R. Brown et al., J. Pharm. Pharmacol., 42 797 (1990) |
| | G. A. Showell et al., Biorg. Med. Chem, 6 1 (1998) |
| | G. A. Showell et al., Biorg. Med. Chem, 6 1 (1998) |
| | A. Anderson et al., J. Med. Chem., 40 1668 (1997) |
| | Aldrich Chemical Co. |
| | M. Carissimi et al., Farmaco, Ed. Sci. 35 812 (1980) |
| | G. P. Ellis et al., J. Chem. Soc. C 2079 (1971) |

EXAMPLE 1

Synthesis of 1-[5-tert-butyl-2-p-tolyl-2H-pyrazol-3-yl]-3-[4-(2-morpholin-4-yl-ethoxy)naphthalen-1-yl]-urea

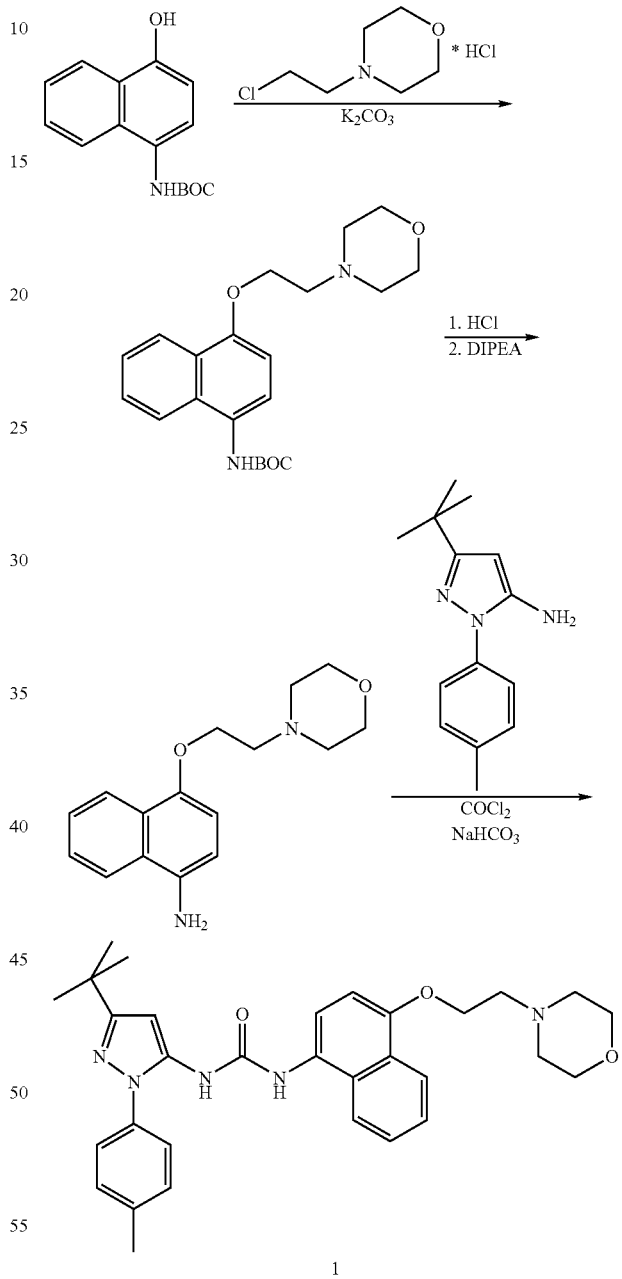

A mixture of 4-N-Boc-amino-1-naphthol (0.464 g), 4-(2-chloroethyl)morpholine hydrochloride (0.3435 g) and powdered potassium carbonate (0.93 g) was heated in acetonitrile (15 mL) at 80° C. for 3 hours, cooled to room temperature and diluted with ethyl acetate and water. The organic layer was washed with water, brine, dried (MgSO$_4$) and the volatiles removed in vacuo. Purification of the residue by flash chromatography using 12% hexanes in ethyl acetate as the eluent and concentration in vacuo of the product-rich fractions afforded the desired 4-N-Boc-aminonaphthyl ether.

A solution of the above 4-N-Boc-aminonaphthyl ether (0.511 g) and HCl (1 mL of a 4 M dioxane solution) in 5 mL dioxane was stirred at room temperature 20 hours. Removal of the volatiles in vacuo provided the desired 4-aminonaphthyl ether. To a solution of 5-amino-3-t-butyl-1-(4-methylphenyl)pyrazole (0.15 g), saturated NaHCO$_3$ (15 mL), and dichloromethane (15 mL) at 0° C. was added phosgene (1.17 mL, 1.93M in toluene). The mixture was stirred for 15 minutes, the organic layer dried (MgSO$_4$) and the volatiles removed in vacuo. The residue was added to a solution of the above 4-aminonaphthyl ether (0.15 g) and diisopropylethyl amine (0.32 mL) in 10 mL THF and the mixture stirred overnight. Ethyl acetate and water were added and the organic layer washed with water, brine and dried (MgSO$_4$). Removal of the volatile in vacuo, purification of the residue by flash chromatography using ethyl acetate as the eluent and concentration in vacuo of the product-rich fractions, followed by recrystallization from hexanes and ethyl acetate provided the title compound.

The following compounds may be made following the procedure described in the above example by using the appropriate morpholine intermediate from Table 1. Using a procedure described by described by T. Watanabe et al. (*Chem. Pharm Bull.* 45, 996 (1997)), treatment of the morpholine analog from Table 1 with chloroacetaldehyde in water, acetic acid and methylene chloride in the presence of sodium triacetoxyborohydride provides the desired chloroethylmorpholine intermediate used in the synthesis.

4-(2-{4-[3-(5-tert-Butyl-2-p-tolyl-2H-pyrazol-3-yl)-ureido]-naphthalen-1-yloxy}-ethyl)-morpholine-2-carboxylic acid methylamide;

4-(2-{4-[3-(5-tert-Butyl-2-p-tolyl-2H-pyrazol-3-yl)-ureido]-naphthalen-1-yloxy}-ethyl carboxylic acid methylphenylamide;

4-(2-{4-[3-(5-tert-Butyl-2-p-tolyl-2H-pyrazol-3-yl)-ureido]-naphthalen-1-yloxy}-ethyl)-morpholine-2-carboxylic acid dimethylamide;

4-(2-{4-[3-(5-tert-Butyl-2-p-tolyl-2H-pyrazol-3-yl)-ureido]-naphthalen-1-yloxy}-ethyl)-morpholine-2-carboxylic acid phenylamide;

2-[4-(2-{4-[3-(5-tert-Butyl-2-p-tolyl-2H-pyrazol-3-yl)-ureido]-naphthalen-1-yloxy}-ethyl)-morpholin-2-yl]-N,N-dimethyl-acetamide;

1-(5-tert-Butyl-2-p-tolyl-2H-pyrazol-3-yl)-3-{4-[2-(2-phenyl-morpholin-4-yl)-ethoxy]-naphthalen-1-yl}-urea;

1-{4-[2-(2-Benzyl-morpholin-4-yl)-ethoxy]-naphthalen-1-yl}-3-(5-tert-butyl-2-p-tolyl-2H-pyrazol-3-yl)-urea;

1-(5-tert-Butyl-2-p-tolyl-2H-pyrazol-3-yl)-3-{4-[2-(2-phenethyl-morpholin-4-yl)-ethoxy]-naphthalen-1-yl}-urea;

1-(5-tert-Butyl-2-p-tolyl-2H-pyrazol-3-yl)-3-{4-[2-(2-phenoxymethyl-morpholin-4-yl)-ethoxy]-naphthalen-1-yl}-urea;

1-(5-tert-Butyl-2-p-tolyl-2H-pyrazol-3-yl)-3-(4-{2-[2-(1-phenyl-ethyl)-morpholin-4-yl]-ethoxy}-naphthalen-1-yl)-urea;

1-(5-tert-Butyl-2-p-tolyl-2H-pyrazol-3-yl)-3-{4-[2-(2-oxa-5-aza-bicyclo[2.2.1]hept-5-yl)-ethoxy]-naphthalen-1-yl}-urea;

1-(5-tert-Butyl-2-p-tolyl-2H-pyrazol-3-yl)-3-{4-[2-(2-thiazol-2-yl-morpholin-4-yl)-ethoxy]-naphthalen-1-yl}-urea;

1-(5-tert-Butyl-2-p-tolyl-2H-pyrazol-3-yl)-3-{4-[2-(2,3-dihydro-benzo[1,4]oxazin-4-yl)-ethoxy]-naphthalen-1-yl}-urea;

EXAMPLE 2

Synthesis of 1-[5-tert-butyl-2-(2-methylpyridin-5-yl)-2H-pyrazol-3-yl]-3-[4-(2-morpholin-4-yl-ethoxy) naphthalen-1-yl]-urea

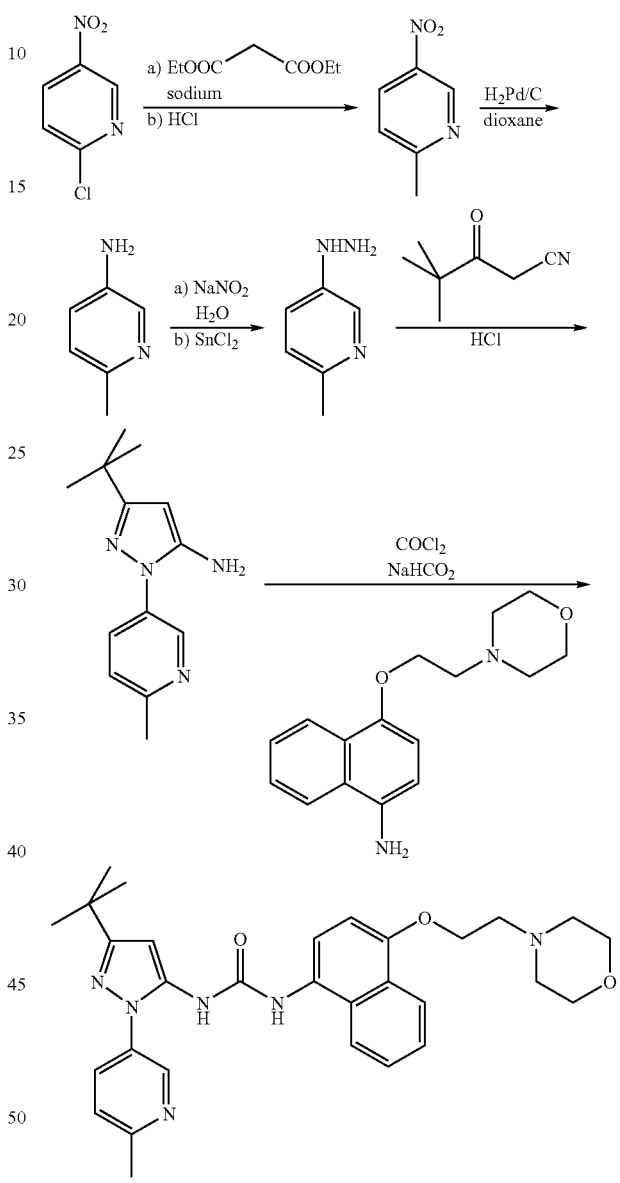

A slurry of diethyl malonate (42 mL) and sodium (4.71 g) were warmed slowly to 90° C. and stirred at 90° C. for 2 hours and 120° C. for 30 minutes before being cooled to room temperature. Toluene (200 mL) and 2-chloro-5-nitropyridine (25.0 g) were added and the mixture was heated at 110° C. for 1.5 hours and ambient temperature for 17 h. After removal of the volatiles in vacuo, 6 N HCl (200 mL) was added and the mixture was heated to reflux for 4 h and cooled to room temperature. The solution was neutralized with solid sodium carbonate, extracted with ethyl acetate (6×100 mL), dried over solid magnesium sulfate, and concentrated to a dark solid. This material was purified by flash chromatography using 20% ethyl acetate in petroleum ether as the eluent. Concentration in vacuo of the product-rich fractions afforded 2-methyl-5-nitropyridine. A mixture of 2-methyl-5-nitropyridine (13.0 g) and 10% Pd on activated carbon (0.1 g) in 1,4-dioxane (150 mL) was hydrogenation at 50 psi for 24 hours and filtered over diatomaceous earth. Removal of the volatiles in vacuo provided 5-amino-2-methylpyridine. A solution of 5-amino-2-methylpyridine (9.90 g) was dissolved in 6 N HCl (100 mL), cooled to 0° C., and vigorously stirred throughout the procedure. Sodium nitrite (6.32 g) in water (50 mL) was added. After 30 minutes, tin (II) chloride dihydrate (52.0 g) in 6 N HCl (100 mL) was added and the reaction slurry was stirred at 0° C. for 3 hours. The pH was adjusted to pH 14 with 40% aqueous potassium hydroxide solution and extracted with ethyl acetate. The combined organic extracts were dried (MgSO$_4$) and removal of the volatiles in vacuo provided 5-hydrazino-2-methylpyridine. A solution of 5-hydrazino-2-methylpyridine (8.0 g) and 4,4-dimethyl-3-oxopentanenitrile (10.0 g) in ethanol (200 mL) and 6 N HCl (6 mL) was refluxed for 17 hours and cooled to room temperature. Solid sodium hydrogen carbonate was added to neutralize the solution. The slurry was filtered and removal of the volatiles in vacuo provided a residue which was purified by column chromatography using ethyl acetate as the eluent. Concentration in vacuo of the product-rich fractions afforded 5-amino-3-t-butyl-1-(2-methylpyridin-5-yl)pyrazole. To a 0° C. mixture of 3 (0.40 g) in dichloromethane (20 mL) and saturated aqueous sodium bicarbonate (20 mL) was added phosgene (1.93 M in toluene, 1.50 mL). The mixture was stirred 15 min and the organic layer was dried (MgSO$_4$) and most of the volatiles removed in vacuo. A solution of the 4-aminonaphthyl ether intermediate from Example 1 (0.30 g) in dichloromethane (10 mL) was added and the mixture stirred for 17 hours at ambient temperature. Removal of the volatiles in vacuo provided a residue that was purified by column chromatography using 10% methanol in ethyl acetate as the eluent. Concentration in vacuo of the product-rich fractions and recrystallization from warm tetrahydrofuran/petroleum ether afforded the title compound.

The following compounds may be made following the procedure described in the above example by using the appropriate morpholine intermediate from Table 1. Using a procedure described by described by T. Watanabe et al. (*Chem. Pharm Bull.* 45, 996 (1997)), treatment of the morpholine analog from Table 1 with chloroacetaldehyde in water, acetic acid and methylene chloride in the presence of sodium triacetoxyborohydride provides the desired chloroethylmorpholine intermediate used in the synthesis.

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methyl amide;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methyl-phenyl-amide;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid dimethylamide;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid phenylamide;

2-{4-[2-(4-{3-[5-tert-Butyl-2-(6-methyl-pyridin-3-yl)-2H-pyrazol-3-yl]-ureido}-naphthalen-1-yloxy)-ethyl]-morpholin-2-yl}-N,N-dimethyl-acetamide;

1-[5-tert-Butyl-2-(6-methyl-pyridin-3-yl)-2H-pyrazol-3-yl]-3-{4-[2-(2-phenyl-morpholin-4-yl)-ethoxy]-naphthalen-1-yl}-urea;

1-{4-[2-(2-Benzyl-morpholin-4-yl)-ethoxy]-naphthalen-1-yl}-3-[5-tert-butyl-2-(6-methyl-pyridin-3-yl)-2H-pyrazol-3-yl]-urea;

1-[5-tert-Butyl-2-(6-methyl-pyridin-3-yl)-2H-pyrazol-3-yl]-3-{4-[2-(2-phenethyl-morpholin-4-yl)-ethoxy]-naphthalen-1-yl}-urea;

1-[5-tert-Butyl-2-(6-methyl-pyridin-3-yl)-2H-pyrazol-3-yl]-3-{4-[2-(2-phenoxymethyl-morpholin-4-yl)-ethoxy]-naphthalen-1-yl}-urea;

1-[5-tert-Butyl-2-(6-methyl-pyridin-3-yl)-2H-pyrazol-3-yl]-3-(4-{2-[2-(1-phenyl-ethyl)-morpholin-4-yl]-ethoxy}-naphthalen-1-yl)-urea;

1-[5-tert-Butyl-2-(6-methyl-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;

1-[5-tert-Butyl-2-(6-methyl-pyridin-3-yl)-2H-pyrazol-3-yl]-3-{4-[2-(2-thiazol-2-yl-morpholin-4-yl)-ethoxy]-naphthalen-1-yl}-urea;

4-(2-{4-[3-(5-tert-Butyl-2-(6-methoxypyridin-3-yl)-2H-pyrazol-3-yl)-ureido]-naphthalen-1-yloxy}-ethyl)-morpholine-2-carboxylic acid methylamide;

4-(2-{4-[3-(5-tert-Butyl-2-(6-methoxypyridin-3-yl)-2H-pyrazol-3-yl)-ureido]-naphthalen-1-yloxy}-ethyl)-morpholine-2-carboxylic acid methyl-phenyl-amide;

4-(2-{4-[3-(5-tert-Butyl-2-(6-methoxypyridin-3-yl)-2H-pyrazol-3-yl)-ureido]-naphthalen-1-yloxy}-ethyl)-morpholine-2-carboxylic acid methylamide;

4-(2-{4-[3-(5-tert-Butyl-2-(6-methoxypyridin-3-yl)-2H-pyrazol-3-yl)-ureido]-naphthalen-1-yloxy}-ethyl)-morpholine-2-carboxylic acid methyl-phenylamide;

4-(2-{4-[3-(5-tert-Butyl-2-(6-methoxypyridin-3-yl)-2H-pyrazol-3-yl)-ureido]-naphthalen-1-yloxy}-ethyl)-morpholine-2-carboxylic acid dimethylamide;

4-(2-{4-[3-(5-tert-Butyl-2-(6-methoxypyridin-3-yl)-2H-pyrazol-3-yl)-ureido]-naphthalen-1-yloxy}-ethyl)-morpholine-2-carboxylic acid phenylamide;

2-[4-(2-{4-[3-(5-tert-Butyl-2-(6-methoxypyridin-3-yl)-2H-pyrazol-3-yl)-ureido]-naphthalen-1-yloxy}-ethyl)-morpholin-2-yl]-N,N-dimethyl-acetamide;

1-[5-tert-Butyl-2-(6-methyl-pyridin-3-yl)-2H-pyrazol-3-yl]-3-{4-[2-(2,3-dihydro-benzo[1,4]oxazin-4-yl)-ethoxy]-naphthalen-1-yl}-urea. The following compound may be made using the by the same procedure but using 5-amino-3-t-butyl-1-(2-methoxypyridin-5-yl)pyrazole in place of 5-amino-3-t-butyl-1-(2-methylpyridin-5yl)pyrazole:

1-(5-tert-Butyl-2-(6-methoxypyridin-3-yl)-2H-pyrazol-3-yl)-3-{4-[2-(2-oxa-5-aza-bicyclo[2.2.1]hept-5-yl)-ethoxy]-naphthalen-1-yl}-urea.

EXAMPLE 3

Synthesis of 1-[5-tert-butyl-2-methyl-2H-pyrazol-3-yl]-3-[4-(2-morpholin-4-yl-ethoxy)naphthalen-1-yl]-urea

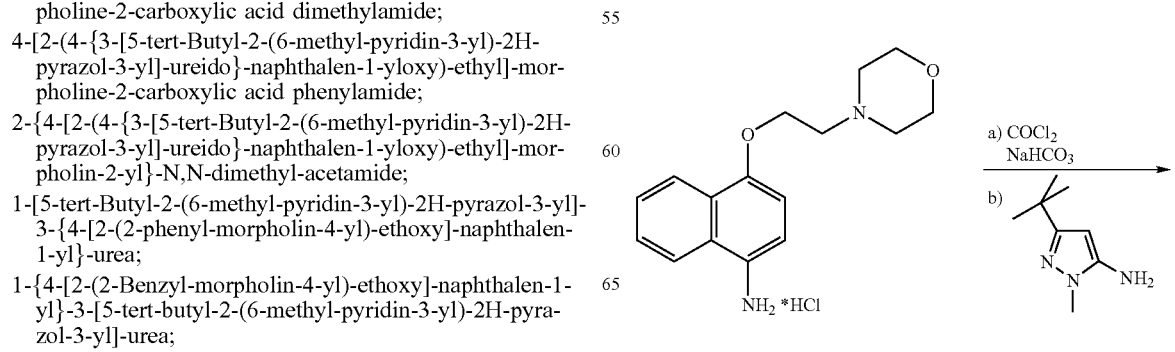

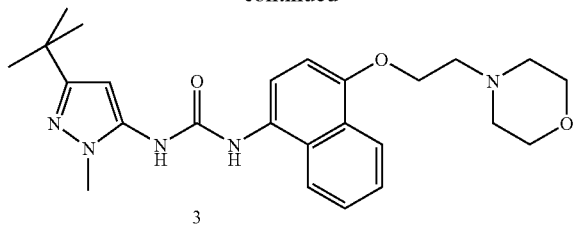

To a mixture of 4-aminonaphthyl ether intermediate from Example 1 (0.40 g) in dichloromethane (35 mL) and saturated aqueous sodium bicarbonate (35 mL) at 0° C., phosgene (1.93 M in toluene, 1.5 mL) was added. The mixture was stirred 15 minutes and the organic layer was dried (MgSO$_4$) and most of the volatiles removed in vacuo. A solution of 5-amino-3-tert-butyl-1-methylpyrazole (0.20 g) in dichloromethane was added and the mixture was stirred for 17 hours at ambient temperature. Removal of the volatiles in vacuo provided a residue that was purified by column chromatography using 10% methanol in ethyl acetate as the eluent. Concentration in vacuo of the product-rich fractions and recrystallization from warm ethyl acetate afforded the title compound.

The following compounds may be made following the procedure described in the above example by using the appropriate morpholine intermediate from Table 1. Using a procedure described by described by T. Watanabe et al. (*Chem. Pharm Bull.* 45, 996 (1997)), treatment of the morpholine analog from Table 1 with chloroacetaldehyde in water, acetic acid and methylene chloride in the presence of sodium triacetoxyborohydride provides the desired chloroethylmorpholine intermediate used in the synthesis.

4-(2-{4-[3-(5-tert-Butyl-2-methyl-2H-pyrazol-3-yl)-ureido]-naphthalen-1-yloxy}-ethyl)-morpholine-2-carboxylic acid methylamide;
4-(2-{4-[3-(5-tert-Butyl-2-methyl-2H-pyrazol-3-yl)-ureido]-naphthalen-1-yloxy}-ethyl)-morpholine-2-carboxylic acid methyl-phenyl-amide;
4-(2-{4-[3-(5-tert-Butyl-2-methyl-2H-pyrazol-3-yl)-ureido]-naphthalen-1-yloxy}-ethyl)-morpholine-2-carboxylic acid methylamide;
4-(2-{4-[3-(5-tert-Butyl-2-methyl-2H-pyrazol-3-yl)-ureido]-naphthalen-1-yloxy}-ethyl)-morpholine-2-carboxylic acid methyl-phenylamide;
4-(2-{4-[3-(5-tert-Butyl-2-methyl-2H-pyrazol-3-yl)-ureido]-naphthalen-1-yloxy}-ethyl)-morpholine-2-carboxylic acid dimethylamide;
4-(2-{4-[3-(5-tert-Butyl-2-methyl-2H-pyrazol-3-yl)-ureido]-naphthalen-1-yloxy}-ethyl)-morpholine-2-carboxylic acid phenylamide;
2-[4-(2-{4-[3-(5-tert-Butyl-2-methyl-2H-pyrazol-3-yl)-ureido]-naphthalen-1-yloxy}-ethyl)-morpholin-2-yl]-N,N-dimethyl-acetamide;
1-(5-tert-Butyl-2-methyl-2H-pyrazol-3-yl)-3-{4-[2-(2-phenyl-morpholin-4-yl)-ethoxy]-naphthalen-1-yl}-urea;
1-{4-[2-(2-Benzyl-morpholin-4-yl)-ethoxy]-naphthalen-1-yl}-3-(5-tert-butyl-2-methyl-2H-pyrazol-3-yl)-urea;
1-(5-tert-Butyl-2-methyl-2H-pyrazol-3-yl)-3-{4-[2-(2-phenethyl-morpholin-4-yl)-ethoxy]-naphthalen-1-yl}-urea;
1-(5-tert-Butyl-2-methyl-2H-pyrazol-3-yl)-3-{4-[2-(2-phenoxymethyl-morpholin-4-yl)-ethoxy]-naphthalen-1-yl}-urea;
1-(5-tert-Butyl-2-methyl-2H-pyrazol-3-yl)-3-(4-{2-[2-(1-phenyl-ethyl)-morpholin-4-yl]-ethoxy}-naphthalen-1-yl)-urea;
1-(5-tert-Butyl-2-methyl-2H-pyrazol-3-yl)-3-{4-[2-(2-thiazol-2-yl-morpholin-4-yl)-ethoxy]-naphthalen-1-yl}-urea;
1-(5-tert-Butyl-2-methyl-2H-pyrazol-3-yl)-3-{4-[2-(2,3-dihydro-benzo[1,4]oxazin-4-yl)-ethoxy]-naphthalen-1-yl}-urea;
1-(5-tert-Butyl-2-methyl-2H-pyrazol-3-yl)-3-{4-[2-(2-oxa-5-aza-bicyclo[2.2.1]hept-5-yl)-ethoxy]-naphthalen-1-yl}-urea;
1-(5-tert-Butyl-2-methyl-2H-pyrazol-3-yl)-3-{4-[2-(2-thiazol-2-yl-morpholin-4-yl)-ethoxy]-naphthalen-1-yl}-urea;
1-(5-tert-Butyl-2-methyl-2H-pyrazol-3-yl)-3-{4-[2-(2,3-dihydro-benzo[1,4]oxazin-4-yl)-ethoxy]-naphthalen-1-yl}-urea.

EXAMPLE 4

Synthesis of 1-(5-tert-butyl-2-methyl-2H-pyrazol-3-yl)-3-{4-[2-(cyclopropylmethyl-amino)-pyrimidin-4-yloxy]-naphthalen-1-yl}-urea

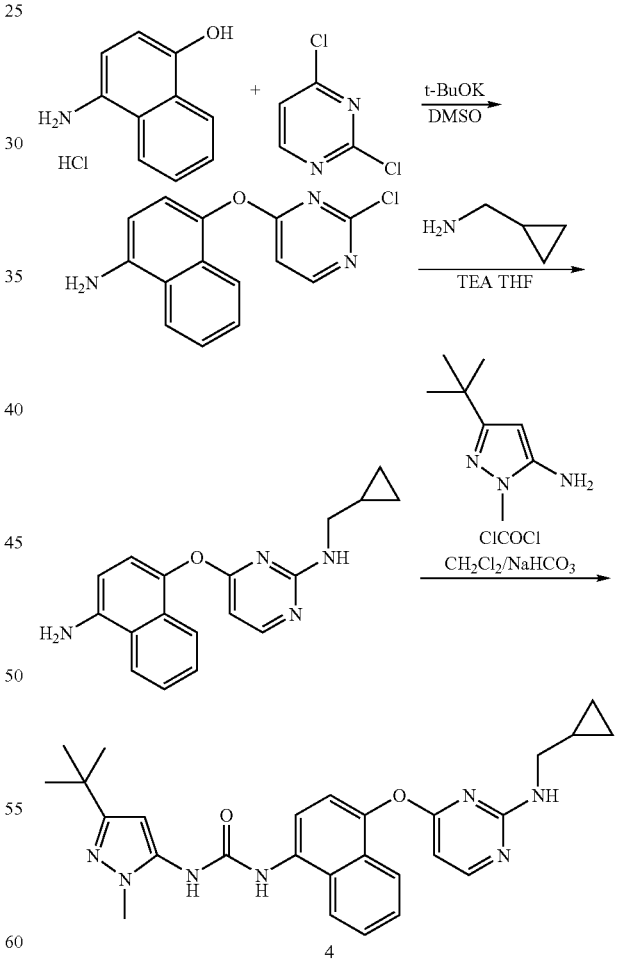

4-Amino-1-naphthol hydrochloride (3.65 g, 16.8 mmol, 1.0 equiv.) was dissolved in 25 mL anhydrous DMSO, then treated with potassium tert-butoxide (3.77 g, 33.6 mmol, 2.0 equiv.) and stirred at room temperature for 30 min. This solution was then added via cannula to a solution of 2,4- dichloropyrimidine (2.5 g, 16.8 mmol, 1.0 equiv.) in 10 mL anhydrous DMSO. The resulting reaction mixture was heated in an oil bath at 70° C. and stirred 2.5 h. The reaction was cooled and partitioned between EtOAc and water. The layers were separated and the aqueous was extracted twice with EtOAc. The combined organic fractions were washed with water and brine, then dried (Na$_2$SO$_4$), filtered and the solvents were removed in vacuo. The aminonaphthyl-chloropyrimidyl ether was purified by column chromatography on silica gel, providing 4.1 g (90%).

The above aminonaphthyl-chloropyrimidyl ether (600 mg, 2.2 mmol), cyclopropane methylamine (0.19 mL, 2.2 mmol) and triethylamine (0.31 mL, 2.2 mmol) were combined in 5 mL anhydrous THF in a sealed tube. The mixture was placed in a 70° C. oil bath and stirred overnight. The reaction was then cooled and partitioned between EtOAc and water. The layers were separated and the aqueous was extracted once with EtOAc.

The combined organic fractions were washed with brine, then dried (Na$_2$SO$_4$), filtered and the solvents were removed in vacuo. The product was purified by column chromatography on silica gel, providing 337 mg (50%) of the desired cyclopropylmethylaminopyrimidine-ether.

3-Amino-5-tert-butyl-2-methyl-2H-pyrazole (80 mg, 0.522 mmol, 1.0 equiv.) was dissolved in 2.0 mL methylene chloride and 2.0 mL saturated aqueous NaHCO$_3$ solution was added. The biphasic mixture was cooled to 0° C., then the organic layer was treated with phosgene in one portion via syringe while not stirring (0.91 mL of a 20% solution toluene, 1.83 mmol, 3.5 equiv.). The resulting mixture was stirred vigorously at 0° C. for 1 h. The organic layer was separated, dried (Na$_2$SO$_4$) and filtered. The methylene chloride was removed in vacuo and the isocyanate in toluene was treated with a solution the above cyclopropylmethylaminopyrimidine-ether (160 mg, 0.522 mmol, 1.0 equiv.) in 4.0 mL anhydrous THF. The mixture was stirred at room temperature overnight, then the solvent was removed in vacuo. The product urea was purified by column chromatography on silica gel using 20–65% EtOAc in hexanes, followed by recrystallization from ether, providing 40 mg (16%) of the title compound.

EXAMPLE 5

Synthesis of 1-[5-tert-butyl-2-(2-methylpyrimidin-5-yl)-2H-pyrazol-3-yl)-3-{4-[2-(cyclopropylmethyl-amino)-pyrimidin-4-yloxy]-naphthalen-1-yl}-urea

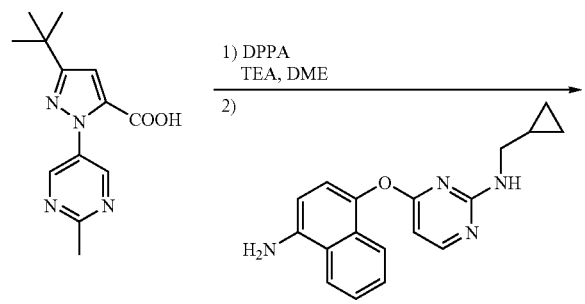

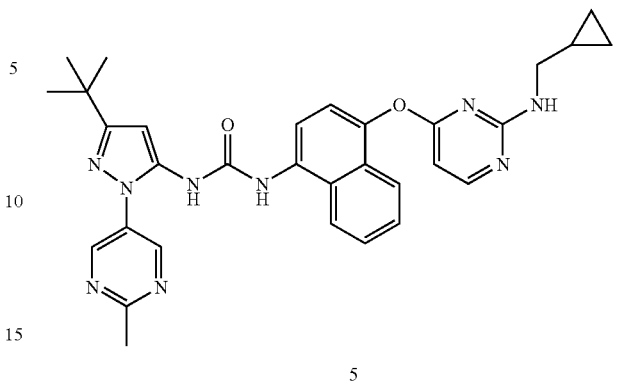

Diphenylphosphoryl azide (DPPA) (0.09 mL, 0.423 mmol, 1.1 equiv.) and triethylamine (0.075 mL, 0.54 mmol, 1.4 equiv.) were added to 5-tert-butyl-2-(2-methylpyrimidin-5-yl)-2H-pyrazole-3-carboxylic acid (100 mg, 0.384 mmol, 1.0 equiv.) in 2.0 mL anhydrous dimethoxyethane in a sealed tube. The mixture was heated at 85° C. for 2.5 h, then a solution of the cyclopropylmethylaminopyrimidine-ether intermediate (see Example 4)(118 mg, 0.38 mmol, 1.0 equiv.) in 3.0 mL anhydrous THF was added and the resulting mixture stirred at room temperature overnight. The solvent was removed in vacuo and the crude urea was purified by column chromatography on silica gel using 0–65% EtOAc in hexanes eluent mixtures. The product was purified further by prep-HPLC affording 15 mg of the title compound (7% yield).

EXAMPLE 6

Synthesis of 1-(5-tert-butyl-2-p-tolyl-2H-pyrazol-3-yl)-3-{4-[2-(cyclopropylmethyl-amino)-pyrimidin-4-yloxy]-naphthalen-1-yl}-urea

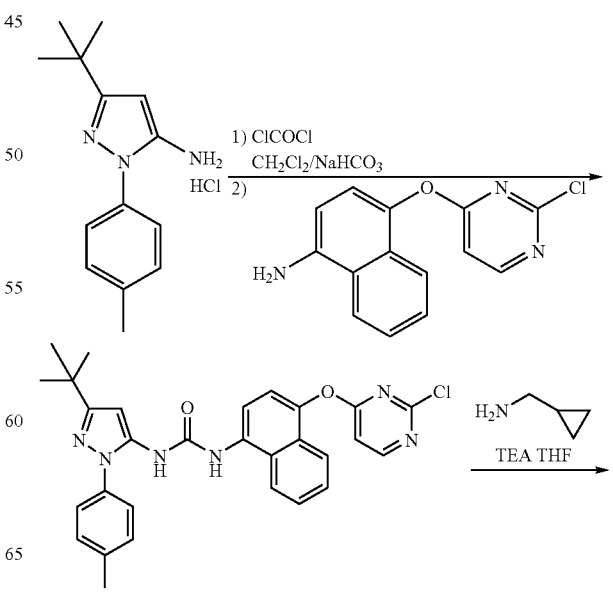

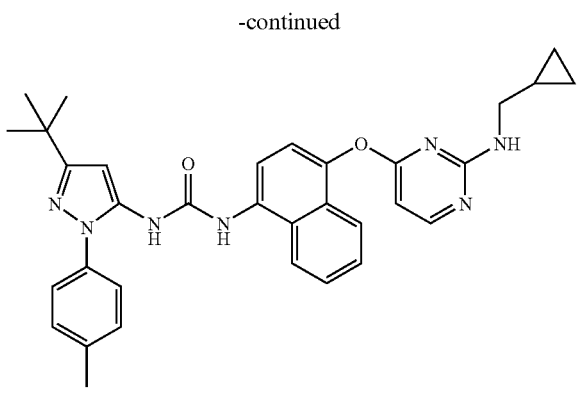

6

3-Amino-5-tert-butyl-2-(p-tolyl)-2H-pyrazole (2.39 g, 9.00 mmol, 1 equiv.) was dissolved in 35 mL methylene chloride and 35 mL saturated aqueous NaHCO$_3$ was added. The biphasic mixture was stirred until all solids had completely dissolved and was then cooled to 0° C. The organic layer was then treated with phosgene in one portion via syringe while not stirring (15.8 mL of a 20% solution toluene, 31.5 mmol, 3.5 equiv.). The resulting mixture was stirred vigorously at 0° C. for 1 h. The organic layer was separated, dried (Na$_2$SO$_4$) and filtered. The methylene chloride was removed in vacuo and the resulting isocyanate in toluene was treated with a solution of aminonaphthyl-chloropyrimidyl ether intermediate (see Example 4) (2.45 g, 9.0 mmol, 1.0 equiv.) in 40 mL anhydrous THF. The mixture was stirred at room temperature for 3.5 h, then the solvent was removed in vacuo. The residue was purified by column chromatography on silica gel using 0–10% MeOH in methylene chloride eluent mixtures, followed by recrystallization from ether, providing 1.90 g (40%) of the urea intermediate.

Cyclopropane methylamine (0.012 mL, 0.13 mmol), triethylamine (0.019 mL, 0.13 mmol) and the above urea intermediate (70 mg, 0.13 mmol) were combined in 1.5 mL anhydrous THF in a sealed tube. The mixture was heated in a 70° C. oil bath for 12 h. The solvent was then removed in vacuo and the residue purified by column chromatography on silica gel using 0–10% MeOH in methylene chloride eluent mixtures. Preparatory reverse-phase HPLC finally afforded 11 mg of the title compound (15% yield).

EXAMPLE 7

Synthesis of 1-(5-tert-butyl-2-methyl-2H-pyrazol-3-yl)-3-{4-[2-(cyclopropylmethyl-amino)-6-methyl-pyrimidin-4-yloxy]-naphthalen-1-yl}-urea

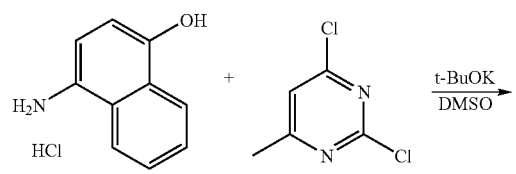

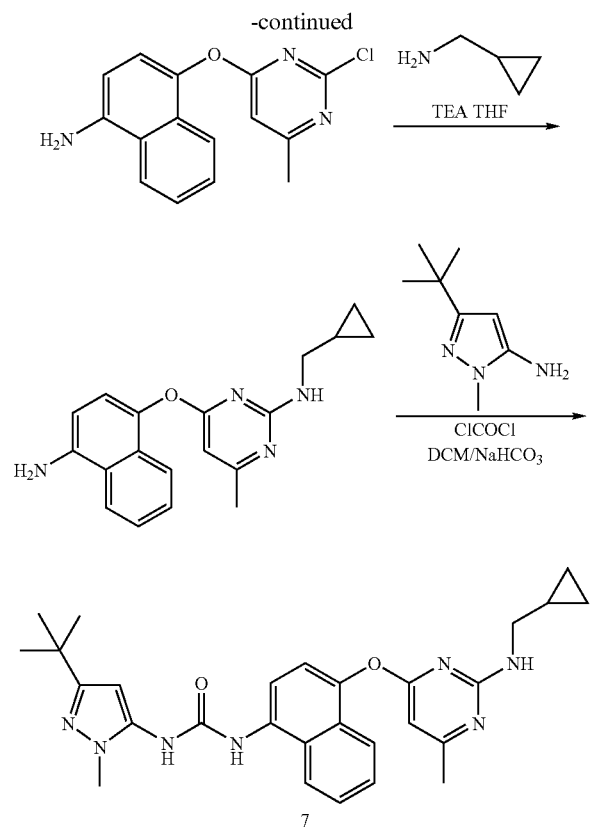

7

4-Amino-1-naphthol hydrochloride (4.00 g, 18.4 mmol, 1.0 equiv.) was dissolved in 25 mL anhydrous DMSO, then treated with potassium tert-butoxide (4.13 g, 36.8 mmol, 2.0 equiv.) and stirred at room temperature for 30 min. This solution was then added via cannula to a solution of 2,4-dichloro-6-methyl-pyrimidine (3.00 g, 18.4 mmol, 1.0 equiv.) in 10 mL anhydrous DMSO. The resulting reaction mixture was heated in an oil bath at 70° C. and stirred 2.5 h. The reaction was cooled and partitioned between EtOAc and water. The layers were separated and the aqueous was extracted twice with EtOAc. The combined organic fractions were washed with water and brine, then dried (Na$_2$SO$_4$), filtered and the solvents were removed in vacuo. The 4-aminonaphthyloxy-2-chloro-6-methylpyrimidine was purified by column chromatography on silica gel using 0–60% EtOAc in hexanes eluent mixtures, providing 4.68 g (89%).

4-Aminonaphthyloxy-2-chloro-6-methylpyrimidine (1.00 g, 3.5 mmol), cyclopropane methylamine (0.30 mL, 3.5 mmol) and triethylamine (0.49 mL, 3.5 mmol) were combined in 10 mL anhydrous THF in a sealed tube. The mixture was placed in a 70° C. oil bath and stirred overnight. The reaction was cooled and partitioned between EtOAc and water. The layers were separated and the aqueous was extracted once with EtOAc. The combined organic fractions were washed with brine, then dried (Na$_2$SO$_4$), filtered and the solvents were removed in vacuo. The product was purified by column chromatography on silica gel using 0–10% MeOH in methylene chloride eluent mixtures, providing 504 mg (45%) of the desired cyclopropylmethylaminopyrimidine-ether.

3-Amino-5-tert-butyl-2-methyl-2H-pyrazole (90 mg, 0.59 mmol, 1.0 equiv.) was dissolved in 2.0 mL methylene chloride and 2.0 mL saturated aqueous NaHCO$_3$ solution was added. The biphasic mixture was cooled to 0° C., then the organic layer was treated with phosgene in one portion via syringe while not stirring (1.03 mL of a 20% solution toluene, 2.06 mmol, 3.5 equiv.). The resulting mixture was stirred vigorously at 0° C. for 1 h. The organic layer was separated, dried (Na₂SO₄) and filtered. The methylene chloride was removed in vacuo and the isocyanate in toluene was treated with a solution of the cyclopropylmethylaminopyrimidine-ether intermediate from above (189 mg, 0.59 mmol, 1.0 equiv.) in 4.0 mL anhydrous THF. The mixture was stirred at room temperature overnight, then the solvent was removed in vacuo. The product urea was purified by column chromatography on silica gel using 20–65% EtOAc in hexanes, followed by recrystallization from ether, providing 165 mg (56%) of the title compound.

EXAMPLE 8

Synthesis of 1-[5-tert-butyl-2-(2-methylpyrimidin-5-yl)-2H-pyrazol-3-yl]-3-{4-[2-(cyclopropylmethyl-amino)-6-methyl-pyrimidin-4-yloxy]-naphthalen-1-yl}-urea

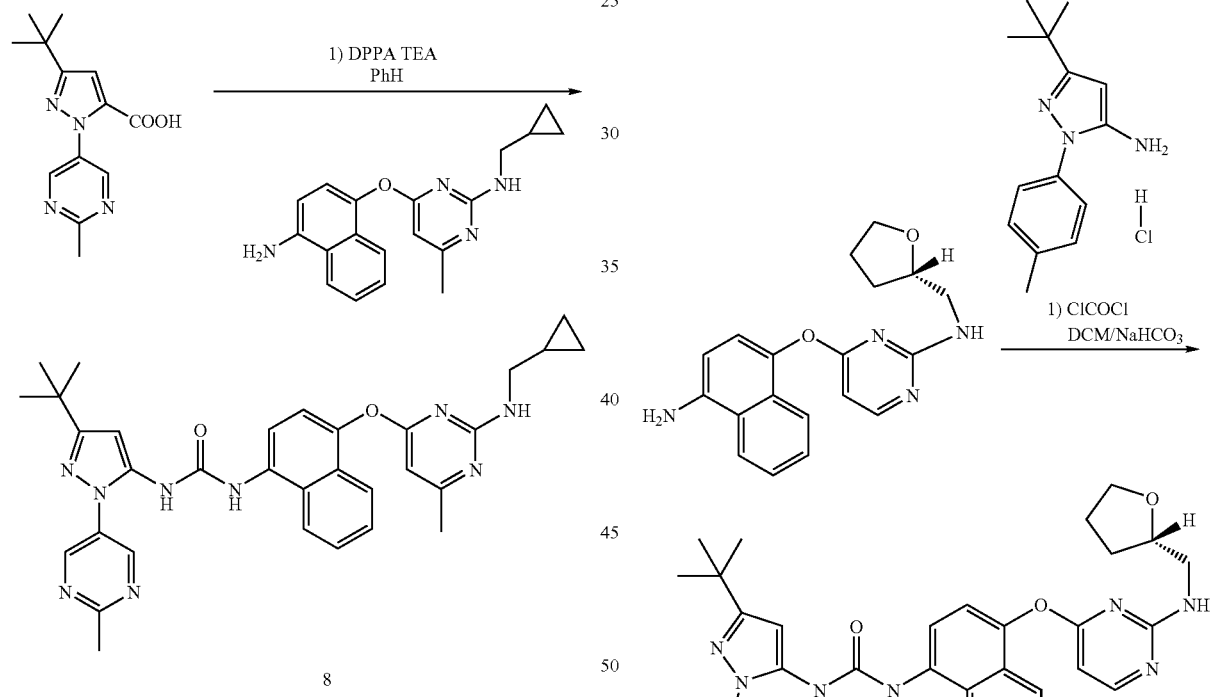

5-tert-Butyl-2-(2-methylpyrimidin-5-yl)-2H-pyrazol-3-carboxylic acid (100 mg, 0.38 mmol, 1 equiv.), DPPA (0.12 mL, 0.57 mmol, 1.5 equiv.) and triethylamine (0.09 mL, 0.65 mmol, 1.7 equiv.) were combined in 5.0 mL benzene and the reaction mixture was stirred at room temperature for 5 h. The resulting homogeneous solution was transferred to a separatory funnel and washed twice with 10 mL of saturated aqueous NaHCO₃ solution. It was also washed once with brine, then dried (MgSO₄), filtered and then transferred to a sealed tube in the presence of the naphthylamine intermediate (123 mg, 0.38 mmol, 1.0 equiv.). A little benzene and methylene chloride (~1 mL of each) were added to help dissolution of reagents. The sealed tube was placed in a 90° C. oil bath and stirred for 12 h. After cooling, the solvents were removed in vacuo and the crude material was purified by column chromatography on silica gel using EtOAc in hexanes eluent mixtures. Recrystallization from acetonitrile afforded 142 mg of the title compound as a white solid.

EXAMPLE 9

Syntheses of 1-(5-tert-butyl-2-p-tolyl-2H-pyrazol-3-yl)-3-(4-{2-[(tetrahydrofuran-2-ylmethyl)-amino]-pyrimidin-4-yloxy}-naphthalen-1-yl)-urea (Both Enantiomers)

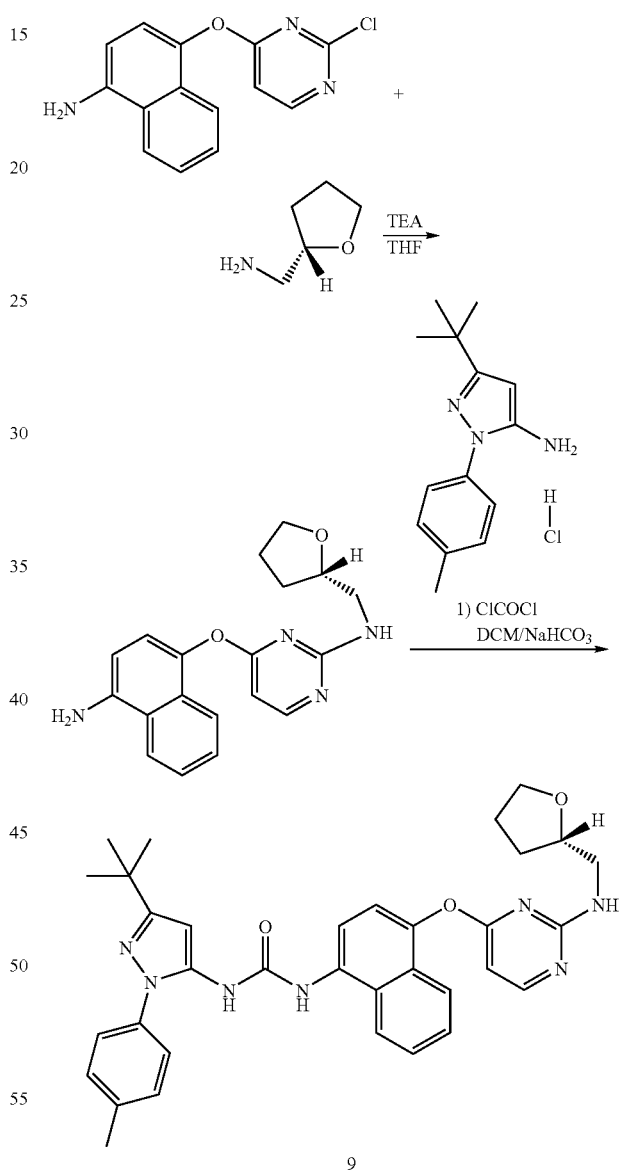

Aminonaphthyl-chloropyrimidyl ether intermediate (see Example 4) (338 mg, 1.24 mmol, 1.0 equiv.) was dissolved in 3.5 mL anhydrous THF in a sealed tube and treated with triethylamine (0.18 mL, 1.30 mmol) and (S)-tetrahydrofurfurylamine (0.13 mL, 1.24 mmol). The mixture was heated to 75° C. for 18 h. The crude solution of product was then cooled and partitioned between water and EtOAc. The separated organic layer was washed with brine and dried (Na$_2$SO$_4$), and filtered. The product was purified by column chromatography on silica gel using MeOH in methylene chloride eluent mixtures providing the desired tetrahydrofuranylmethylaminopyrimidine ether intermediate as a pink foam (278 mg, 66%).

In a similar way the (R)-enantiomer of tetrahydrofurfurylamine (0.13 mL) to afforded the opposite enantiomer in 76% yield.

3-Amino-5-tert-butyl-2-(p-tolyl)-2H-pyrazole hydrochloride (59 mg, 0.22 mmol, 1 equiv.) was dissolved in 12 mL methylene chloride and 12 mL saturated aqueous NaHCO$_3$ was added. The biphasic mixture was stirred until all solids had completely dissolved and cooled to 0° C. The organic layer was then treated with phosgene in one portion via syringe while not stirring (0.40 mL of a 20% solution toluene, 0.78 mmol, 3.5 equiv.). The resulting mixture was stirred vigorously at 0° C. for 0.5 h. The organic layer was separated, dried (Na$_2$SO$_4$) and filtered. The methylene chloride was removed in vacuo and the resulting isocyanate in toluene was treated with a solution of the above tetrahydrofuranylmethylaminopyrimidine ether intermediate (75 mg, 0.22 mmol, 1.0 equiv.) in 4 mL anhydrous THF. The mixture was stirred at room temperature for 36 h, then the solvent was removed in vacuo. The product urea was purified by column chromatography on silica gel using 0–10% MeOH in methylene chloride eluent mixtures, affording 112 mg of the title compound [(S)-enantiomer] as a light pink foam. Further purification by preparatory reverse-phase HPLC afforded 44 mg of the title compound as a pure, yellow foam.

The synthesis of the (R)-enantiomer was achieved following exactly the same procedure as outlined above, using the opposite enantiomer of the intermediate tetrahydrofuranylmethylaminopyrimidine ether intermediate.

Assessment of Biological Properties

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% CO$_2$ prior to stimulation with lipopolysaccharide (LPS; 1 μg/ml final; Siga L-2630, from *E.coli* serotype 0111.B4; stored as 1 mg/ml stock in endotoxin screened distilled H$_2$O at −80° C.). Blanks (unstimulated) received H$_2$O vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC50 value is the concentration of the test compound that caused a 50% decrease in the maximal TNFα production.

Preferred compounds will have an IC$_{50}$<10 uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

What is claimed is:

1. A compound chosen from:
   1-(5-tert-Butyl-2-p-tolyl-2H-pyrazol-3-yl)-3-(4-{2-[2-(1-phenyl-ethylamino)-pyrimidin-4-yl]-ethoxy}-naphthalen-1-yl)-urea;
   1-(5-tert-Butyl-2-p-tolyl-2H-pyrazol-3-yl)-3-{4-[2-(cyclopropylmethyl-amino)-pyrimidin-4-yloxy]-naphthalen-1-yl}-urea;
   1-(5-tert-Butyl-2-p-tolyl-2H-pyrazol-3-yl)-3-(4-{2-[(tetrahydro-furan-2-ylmethyl)-amino]-pyrimidin-4-yloxy}-naphthalen-1-yl)-urea;
   1-(5-tert-Butyl-2-p-tolyl-2H-pyrazol-3-yl)-3-(4-{2-[(thiophen-2-ylmethyl)-amino]-pyrimidin-4-yloxy}-naphthalen-1-yl)-urea;
   1-(5-tert-Butyl-2-p-tolyl-2H-pyrazol-3-yl)-3-(4-{2-[2-(1-pyridin-2-yl-ethylamino)-pyrimidin-4-yl]-ethoxy}-naphthalen-1-yl)-urea;
   4-(2-{4-[3-(5-tert-Butyl-2-p-tolyl-2H-pyrazol-3-yl)-ureido]-naphthalen-1-yloxy}-ethyl)-pyridine-2-carboxylic acid ethylamide;
   4-{4-[3-(5-tert-Butyl-2-p-tolyl-2H-pyrazol-3-yl)-ureido]-naphthalen-1-yloxy}-pyridine-2-carboxylic acid diethylamide;
   1-(5-tert-Butyl-2-p-tolyl-2H-pyrazol-3-yl)-3-{4-[2-(2-piperidin-1-ylmethyl-pyridin-4-yl)-ethoxy]-naphthalen-1-yl}-urea;
   4-(4-{3-[5-tert-Butyl-2-(6-methyl-pyridin-3-yl)-2H-pyrazol-3-yl]-ureido}-naphthalen-1-yloxy)-pyridine-2-carboxylic acid methyl-phenyl-amide;
   1-(5-tert-Butyl-2-p-tolyl-2H-pyrazol-3-yl)-3-(4-{2-[2-(1-phenyl-ethylamino)-pyrimidin-4-yloxy]-ethyl}-naphthalen-1-yl)-urea;
   4-(2-{4-[3-(5-tert-Butyl-2-p-tolyl-2H-pyrazol-3-yl)-ureido]-naphthalen-1-yloxy}-ethyl)-morpholine-2-carboxylic acid ethylamide;
   1(5-tert-Butyl-2-p-tolyl-2H-pyrazol-3-yl)-3-{4-[2-(2-diethylaminomethyl-morpholin-4-yl)-ethoxy]-naphthalen-1-yl}-urea;
   4-(2-{4-[3-(5-tert-Butyl-2-p-tolyl-2H-pyrazol-3-yl)-ureido]-naphthalen-1-yloxy}-ethyl)-morpholine-2-carboxylic acid methyl-phenyl-amide;
   1-(5-tert-Butyl-2-methyl-2H-pyrazol-3-yl)-3-(4-{2-[2-(1-phenyl-ethylamino)-pyrimidin-4-yl]-ethoxy}-naphthalen-1-yl)-urea;
   1-(5-tert-Butyl-2-methyl-2H-pyrazol-3-yl)-3-{4-[2-(cyclopropylmethyl-amino)-pyrimidin-4-yloxy]-naphthalen-1-yl}-urea;
   1-(5-tert-Butyl-2-methyl-2H-pyrazol-3-yl)-3-(4-{2-[(tetrahydro-furan-2-ylmethyl)-amino]-pyrimidin-4-yloxy}-naphthalen-1-yl)-urea;

1-(5-tert-Butyl-2-methyl-2H-pyrazol-3-yl)-3-(4-{2-[(thiophen-2-ylmethyl)-amino]-pyrimidin-4-yloxy}-naphthalen-1-yl)-urea;

1-(5-tert-Butyl-2-methyl-2H-pyrazol-3-yl)-3-(4-{2-[2-(1-pyridin-2-yl-ethylamino)-pyrimidin-4-yl]-ethoxy}-naphthalen-1-yl)-urea;

4-(2-{4-[3-(5-tert-Butyl-2-methyl-2H-pyrazol-3-yl)-ureido]-naphthalen-1-yloxy}-ethyl)-pyridine-2-carboxylic acid ethylamide;

4-{4-[3-(5-tert-Butyl-2-methyl-2H-pyrazol-3-yl)-ureido]-naphthalen-1-yloxy}-pyridine-2-carboxylic acid diethylamide;

1-(5-tert-Butyl-2-methyl-2H-pyrazol-3-yl)-3-{4-[2-(2-piperidin-1-ylmethyl-pyridin-4-yl)-ethoxy]-naphthalen-1-yl}-urea;

1-(5-tert-Butyl-2-methyl-2H-pyrazol-3-yl)-3-(4-{2-[2-(1-phenyl-ethylamino)-pyrimidin-4-yloxy]-ethyl}-naphthalen-1-yl)-urea;

4-(2-{4-[3(5-tert-Butyl-2-methyl-2H-pyrazol-3-yl)-ureido]-naphthalen-1-yloxy}-ethyl)-morpholine-2-carboxylic acid ethylamide;

1-(5-tert-Butyl-2-methyl-2H-pyrazol-3-yl)-3-{4-[2-(2-diethylaminomethyl-morpholin-4-yl)-ethoxy]-naphthalen-1-yl}-urea;

4-(2-{4-[3-(5-tert-Butyl-2-methyl-2H-pyrazol-3-yl)-ureido]-naphthalen-1-yloxy}-ethyl)-morpholine-2-carboxylic acid methyl-phenyl-amide;

4-(2-{4-[3-(5-tert-Butyl-2-p-tolyl-2H-pyrazol-3-yl)-ureido]-naphthalen-1-yloxy}-ethyl)-morpholine-2-carboxylic acid methylamide;

4-(2-{4-[3-(5-tert-Butyl-2-p-tolyl-2H-pyrazol-3-yl)-ureido]-naphthalen-1-yloxy}-ethyl)-morpholine-2-carboxylic acid dimemethylamide;

4-(2-{4-[3-(5-tert-Butyl-2-p-tolyl-2H-pyrazol-3-yl)-ureido]-naphthalen-1-yloxy}-ethyl)-morpholine-2-carboxylic acid phenylamide;

2-[4-(2-{4-[3-(5-tert-Butyl-2-p-tolyl-2H-pyrazol-3-yl)-ureido]-naphthalen-1-yloxy}-ethyl)-morpholin-2-yl]-N,N-dimethyl-acetamide;

1-(5-tert-Butyl-2-p-tolyl-2H-pyrazol-3-yl)-3-{4-[2-(2-phenyl-morpholin-4-yl)-ethoxy]-naphthalen-1-yl}-urea;

1-{4-[2-(2-Benzyl-morpholin-4-yl)-ethoxy]-naphthalen-1-yl}-3-(5-tert-butyl-2-p-tolyl-2H-pyrazol-3-yl)-urea;

1-(5-tert-Butyl-2-p-tolyl-2H-pyrazol-3-yl)-3-{4-[2-(2-phenethyl-morpholin-4-yl)-ethoxy]-naphthalen-1-yl}-urea;

1-(5-tert-Butyl-2-p-tolyl-2H-pyrazol-3-yl)-3-{4-[2-(2-phenoxymethyl-morpholin-4-yl)-ethoxy]-naphthalen-1-yl}-urea;

1-(5-tert-Butyl-2-p-tolyl-2H-pyrazol-3-yl)-3-(4-{2-[2-(1-phenyl-ethyl)-morpholin-4-yl]-ethoxy}-naphthalen-1-yl)-urea;

1-(5-tert-Butyl-2-p-tolyl-2H-pyrazol-3-yl)-3-{4-[2-(2-oxa-5-aza-bicyclo[2.2.1]hept-5-yl)-ethoxy]-naphthalen-1-yl}-urea;

1-(5-tert-Butyl-2-p-tolyl-2H-pyrazol-3-yl)-3-{4-[2-(2-thiazol-2-yl -morpholin-4-yl)-ethoxy]-naphthalen-1-yl}-urea;

1-(5-tert-Butyl-2-p-tolyl-2H-pyrazol-3-yl)-3-{4-[2-(2,3-dihydro-benzo[1,4oxazin-4-yl)-ethoxy]-naphthalen-1-yl}-urea;

4-(2-{4-[3-(5-tert-Butyl-2-methyl-2H-pyrazol-3-yl)-ureido]-naphthalen-1-yloxy}-ethyl)-morpholine-2-carboxylic acid methylamide;

4-(2-{4-[3-(5-tert-Butyl-2-methyl-2H-pyrazol-3-yl)-ureido]-naphthalen-1-yloxy}-ethyl)-morpholine-2-carboxylic acid methylamide;

4-(2-{4-[3-(5-tert-Butyl-2-methyl-2H-pyrazol-3-yl)-ureido]-naphthalen-1-yloxy}-ethyl)-morpholine-2-carboxylic acid dimethylamide;

4-(2-{4-[3-(5-tert-Butyl-2-methyl-2H-pyrazol-3-yl)-ureido]-naphthalen-1-yloxy}-ethyl)-morpholine-2-carboxylic acid phenylamide;

2-[4-(2-{4-[3-(5-tert-Butyl-2-methyl-2H-pyrazol-3-yl)-ureido]-naphthalen-1-yloxy}-ethyl)-morpholine-2-yl]-N,N-dimethyl-acetamide;

1-(5-tert-Butyl-2-methyl-2H-pyrazol-3yl)-3-{4-[2-(2-phenyl-morpholin-4-yl)-ethoxy]-naphthalen-1-yl}-urea;

1-{4-[2-(2-Benzyl-morpholin-4-yl)-ethoxy]-naphthalen-1-yl}-3-(5-tert-butyl-2-methyl-2H-pyrazol-3-yl)-urea;

1-(5-tert-Butyl-2-methyl-2H-pyrazol-3-yl)-3-{4-[2-(2-phenethyl-morpholin-4-yl)-ethoxy]-naphthalen-1-yl}-urea;

1-(5-tert-Butyl-2-methyl-2H-pyrazol-3-yl)-3-{4-[2-(2-phenoxymethyl-morpholin-4-yl)-ethoxy]-naphthalen-1-yl}-urea;

1-(5-tert-Butyl-2-methyl-2H-pyrazol-3-yl)-3-(4-{2-[2-phenyl-ethyl)-morpholin-4-yl]-ethoxy}-naphthalen-1-yl)-urea;

1-(5-tert-Butyl-2-methyl-2H-pyrazol-3-yl)-3-{4-[2-(2-oxa-5-aza-bicyclo[2.2.1]hept-5-yl)-ethoxy]-naphthalen-1-yl}-urea;

1-(5-tert-Butyl-2-methyl-2H-pyrazol-3-yl)-3-{4-[2-(2-thiazol-2-yl-morpholin-4-yl)-ethoxy]-naphthalen-1-yl}-urea;

1-(5-tert-Butyl-2-methyl-2H-pyrazol-3-yl)-3-{4-[2-(2,3-dihydro-benzo[1,4oxazin-4-yl)-ethoxy]-naphthalen-1-yl}-urea;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methylamide;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methyl-phenyl-amide;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid dimethylamide;

4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid phenylamide;

2-{4-[2-(4-{3-[5tert-Butyl-2-(6-methyl-pyridin-3-yl)-2H-pyrazol-3-yl]-ureido}-naphthalen-1-yloxy)-ethyl]-morpholine-2-yl}-N,N-dimethyl-acetamide;

1-[5-tert-Butyl-2-(6-methyl-pyridin-3-yl)-2H-pyrazol-3-yl]-3-{4-[2-(2-phenyl-morpholin-4-yl)-ethoxy]-naphthalen-1-yl}-urea;

1-{4-[2-(2-Benzyl-morpholin-4-yl)-ethoxy]-naphthalen-1-yl}-3-[5-tert-butyl-2-(6-methyl-pyridin-3-yl)-2H-pyrazol-3-yl]-urea;

1-[5-tert-Butyl-2-(6-methyl-pyridin-3-yl)-2H-pyrazol-3-yl]-3-{4-[2-(2-phenethyl-morpholin-4-yl)-ethoxy]-naphthalen-1-yl}-urea;

1-[5-tert-Butyl-2-(6-methyl-pyridin-3-yl)-2H-pyrazol-3-yl]-3-{4-[2-(2-phenoxymethyl-morpholin-4-yl)-ethoxy]-naphthalen-1-yl}-urea;

1-[5-tert-Butyl-2-(6-methyl-pyridin-3-yl)-2H-pyrazol-3-yl]-3-(4-{2-[2-(1-phenyl-ethyl)-morpholin-4-yl]-ethoxy}-naphthalen-1-yl)-urea;

1-[5-tert-Butyl-2-(6-methyl-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;
1-[5-tert-Butyl-2-(6-methyl-pyridin-3-yl)-2H-pyrazol-3-yl]-3-{4-[2-(2-thiazol-2-yl-morpholin-4-yl)-ethoxy]-naphthalen-1-yl}-urea;
1-[5-tert-Butyl-2-(6-methyl-pyridin-3-yl)-2H-pyrazol-3-yl]-3-{4-[2-(2,3-dihydro-benzo[1,4]oxazin-4-yl)-ethoxy]-naphthalen-1-yl}-urea;
1-[5-tert-Butyl-2-(6-methoxy-pyridin-3-yl)-2H-pyrazol-3-yl]-3-{4-[2-(2-phenethyl-morpholin-4-yl)-ethoxy]-naphthalen-1-yl}-urea;
1-[5-tert-Butyl-2-(6-methoxy-pyridin-3-yl)-2H-pyrazol-3-yl]-3-{4-[2-(2-phenoxymethyl-morpholin-4-yl)-ethoxy]-naphthalen-1-yl}-urea;
1-[5-tert-Butyl-2-(6methoxy-pyridin-3-yl)-2H-pyrazol-3-yl]-3-(4-{2-[2-(1-phenyl-ethyl)-morpholin-4-yl)-ethoxy}-naphthalen-1-yl)-urea;
1-[5-tert-Butyl-2-(6-methoxy-pyridin-3-yl)-2H-pyrazol-3-yl]-3-{4-[2-(2-oxa-5aza-bicyclo[2.2.1]hept-5-yl)-ethoxy]-naphthalen-1-yl}-urea;
1-[5-tert-Butyl-2-(6-methoxy-pyridin-3-yl)-2H-pyrazol-3-yl]-3-{4-[2-(2-thiazol-2-yl-morpholin-4-yl)-ethoxy]-naphthalen-1-yl}-urea;
1-[5-tert-Butyl-2-(6-methoxy-pyridin-3-yl)-2H-pyrazol-3-yl]-3-{4-[2-(2,3-dihydro-benzo[1,4]oxazin-4-yl)-ethoxy]-naphthalen-1-yl}-urea;
1(5-tert-Butyl-2-(6-methoxy-pyridin-3-yl)-2H-pyrazol-3-yl)-3-{4-[2-(2,3-dihydro-benzo[1,4]oxazin-4-yl)-ethoxy]-naphthalen-1-yl }-urea;
1-(5-tert-Butyl -2-methyl-2H-pyrazol-3-yl)-3-{4-[2-(cyclopropylmethyl-amino)-6-methyl-pyrimidin-4-yloxy]-naphthalen-1-yl}-urea;
1-(5-tert-Butyl-2-{2-methyl-pyrimidin-5-yl)-3-{4-[2-(cyclopropylmethyl-amino)-pyrimidin-4-yloxy]-ethyl}-naphthalen-1-yl)-urea and
1-(5-tert-Butyl-2-{2-methyl-pyrimidin-5-yl)-3-{4-[2-(cyclopropylmethyl-amino)-6-methyl-pyrimidin-4-yloxy]-ethyl}-naphthalen-1-yl)-urea
or the pharmaceutically acceptable acids or salts thereof.
2. A compound chosen from:
1-(5-tert-Butyl-2-p-tolyl-2H-pyrazol-3-yl)-3-(4-{2-[2-(1-phenyl-ethylamino)-pyrimidin-4-yl]-ethoxy}-naphthalen-1-yl)-urea;
1-(5-tert-Butyl-2-p-tolyl-2H-pyrazol-3-yl)-3-{4-[2-(cyclopropylmethyl-amino)-pyrimidin-4-yloxy]-naphthalen-1-yl}-urea;
1-(5-tert-Butyl-2-p-tolyl-2H-pyrazol-3-yl)-3-(4-{2-[(tetrahydro-furan-2-ylmethyl)-amino]-pyrimidin-4-yloxy}-naphthalen-1-yl)-urea;
1-(5-tert-Butyl-2-p-tolyl-2H-pyrazol-3-yl)-3-(4-{2-[2-(1-pyridin-2-yl-ethylamino)-pyrimidin-4-yl]-ethoxy}-naphthalen-1-yl)-urea;
4-(2-{4-[3-(5-tert-Butyl-2-p-tolyl-2H-pyrazol-3-yl)-ureido]-naphthalen-1-yloxy}-ethyl)-pyridne-2-carboxylic acid ethylamide;
4-{4-[3-(5-tert-Butyl-2-p-tolyl-2H-pyrazol-3-yl)-ureido]-naphthalen-1-yloxy}-pyridine)-2-carboxylic acid diethylamide;
4-(4-{3-[5-tert-Butyl-2-(6methyl-pyridin-3yl)-2H-pyrazol-3-yl]-ureido}-naphthalen-1-yloxy)-pyridine-2-carboxylic acid methyl-phenyl-amide;
4-(2-{4-[3-(5-tert-Butyl-2-p-tolyl-2H-pyrazol-3-yl)-ureido]-naphthalen-1-yloxy}-ethyl)-morpholine-2-carboxylic acid ethylamide;
4-(2-{4-[3-(5-tert-Butyl-2-p-tolyl-2H-pyrazol-3-yl)-ureido]-naphthalen-1-yloxy}-ethyl)-morpholine-2-carboxylic acid methyl-phenyl-amide;
4-(2-{4-[3-(5-tert-Butyl-2-p-tolyl-2H-pyrazol-3-yl)-ureido]-naphthalen-1-yloxy}-ethyl)-morpholine-2-carboxylic acid methylamide;
4-(2-{4-[3-(5-tert-Butyl-2-p-tolyl-2H-pyrazol-3-yl)-ureido]-naphthalen-1-yloxy}-ethyl)-morpholine-2-carboxylic acid dimethylamide;
4-(2-{4-[3-(5-tert-Butyl-2-p-tolyl-2H-pyrazol-3-yl)-ureido]-naphthalen-1-yloxy}-ethyl)-morpholine-2-carboxylic acid phenylamide;
4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methylamide;
4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid methyl-phenyl-amide;
4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid dimethylamide;
4-[2-(4-{3-[5-tert-Butyl-2-(6-methyl-pyridin-3-yl)-2H-pyrazol-3-yl]-ureido}-naphthalen-1-yloxy)-ethyl]-morpholine-2-carboxylic acid phenylamide;
1-{4-[2-(2-Benzyl-morpholin-4-yl)-ethoxy]-naphthalen-1-yl}-3-[5-tert-butyl-2(6-methyl-pyridin-3-yl)-2H-pyrazol-3-yl]-urea;
1-[5-tert-Butyl-2-(6-methyl-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;
1-[5-tert-Butyl-2-(6-methyl-pyridin-3-yl)-2H-pyrazol-3-yl]-3-{4-[2-(2,3-dihydro-benzo[1,4]oxazin-4-yl)-ethoxy]-naphthalen-1-yl}-urea;
1-[5-tert-Butyl-2-(6-methoxy-pyridin-3-yl)-2H-pyrazol-3-yl]-3-{4-[2-(2-oxa-5-aza-bicyclo[2.2.1]hept-5-yl)-ethoxy]-naphthalen-1-yl}-urea;
1-[5-tert-Butyl-2-(6-methoxy-pyridin-3-yl)-2H-pyrazol-3-yl]-3-{4-[2-(2,3-dihydro-benzo[1,4]oxazin-4-yl)-ethoxy]-naphthalen-1-yl}-urea;
1-(5-tert-Butyl-2-{2-methyl-pyrimidin-5-yl)-3-{4-[2-(cyclopropylmethyl-amino)-pyrimidin-4-yloxy]-ethyl}-naphthalen-1-yl)-urea and
1-(5-tert-Butyl-2-{2-methyl-pyrimidin-5-yl)-3-{4-[2-(cyclopropylmethyl-amino)-6-methyl-pyrimidin-4-yloxy]-ethyl}-naphthalen-1-yl)-urea
or the pharmaceutically acceptable acids or salts thereof.
3. A pharmaceutical composition comprising a pharmaceutically effective amount of a compound according to claim 1 and one or more pharmaceutically acceptable carriers and/or adjuvants.
4. A method of treating a disease or condition selected from rheumatoid arthritis, inflammatory bowel disease, osteoarthritis, Crohn3s disease, ulcerative colitis, psoriasis, and chronic obstructive pulmonary disease, said method comprising administering to a patient a pharmaceutically effective amount of a compound according to claim 1.

* * * * *